US012774481B2

(12) United States Patent
Yang et al.

(10) Patent No.: US 12,774,481 B2
(45) Date of Patent: Oct. 27, 2026

(54) COMPOSITIONS, SYSTEMS AND METHODS FOR ATOM TRANSFER RADICAL ADDITION REACTION

(71) Applicant: The Regents of the University of California, Oakland, CA (US)

(72) Inventors: Yang Yang, Goleta, CA (US); Qi Zhou, Goleta, CA (US); Michael Chin, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 308 days.

(21) Appl. No.: 18/294,902

(22) PCT Filed: Aug. 2, 2022

(86) PCT No.: PCT/US2022/074439
§ 371 (c)(1),
(2) Date: Feb. 2, 2024

(87) PCT Pub. No.: WO2023/015191
PCT Pub. Date: Feb. 9, 2023

(65) Prior Publication Data

US 2024/0336943 A1 Oct. 10, 2024

Related U.S. Application Data

(60) Provisional application No. 63/228,562, filed on Aug. 2, 2021.

(51) Int. Cl.
*C12P 17/10* (2006.01)
*C12N 9/02* (2006.01)

(52) U.S. Cl.
CPC ............ *C12P 17/10* (2013.01); *C12N 9/0071* (2013.01); *C12Y 114/14001* (2013.01)

(58) Field of Classification Search
None
See application file for complete search history.

(56) References Cited

U.S. PATENT DOCUMENTS

| | | | | |
|---|---|---|---|---|
| 7,465,567 | B2 * | 12/2008 | Cirino | C12Y 114/14001 435/71.1 |
| 8,741,616 | B2 * | 6/2014 | Arnold | C12N 9/0071 435/71.1 |
| 2010/0240106 | A1 * | 9/2010 | Wong | C12P 7/22 435/189 |
| 2010/0267083 | A1 * | 10/2010 | Hauer | C12P 7/22 435/189 |
| 2019/0211367 | A1 | 7/2019 | Coelho et al. | |
| 2020/0024372 | A1 | 1/2020 | Matyjaszewski et al. | |

OTHER PUBLICATIONS

Bernhardt. J of Biotech 124 p. 128-145 (Year: 2006).*
"International Search Report and Written Opinion Received mailed on Jan. 5, 2023", International Application No. PCT/US2022/74439, 9.
Clark , et al., "Copper Catalyzed Atom Transfer Radical Cyclization Reactions", European Journal of Organic Chemistry, vol. 2016, 2231-2243.
Fu , et al., "Engineered P450 Atom-Transfer Radical Cyclases and Bifunctional Biocatalysts: Reaction Mechanism and Origin of Enatioselectivity", Journal of the American Chemical Society, vol. 144, 13344-13355.
Key , et al., "Beyond Iron: Iridium-Containing P450 Enzymes for Selective Cyclopropanations of Structurally Diverse Alkenes", ACS Central Science, vol. 3, Apr. 1, 2017, 302-308.

* cited by examiner

*Primary Examiner* — Blaine Lankford
(74) *Attorney, Agent, or Firm* — Billion & Armitage

(57) ABSTRACT

Biocatalysts and methods for performing atom transfer radical addition chemistry are described. Generally, modified metalloenzymes are utilized to perform enantioselective and/or diastereoselective atom transfer radical addition chemistry on a broad range of substrates.

20 Claims, 17 Drawing Sheets

Specification includes a Sequence Listing.

$R^1$ is an alkyl group. $R^2$, $R^3$, $R^4$ and $R^5$ is H, alkyl, aryl, acyl, CN, $NO_2$, R'R''N-, or R'O-.
X is a halide.
In some cases, the resulting ATRA product undergoes elimination to provide the corresponding alkene product following the loss of HX.

L = an amino acid residue from the protein scaffold 1a 2a 1 2

2a
8,110 TTN
97:3 e.r.

2b
7,600 TTN
97:3 e.r.

X-ray structure 2c
7,500 TTN
94:6 e.r.

2d
1,640 TTN
85:15 e.r.

2e
890 TTN
92:8 e.r.

2f
7,200 TTN
97:3 e.r.

2g
5,300 TTN
94:6 e.r.

2h
6,900 TTN
93:7 e.r.

2i
2,600 TTN
96:4 e.r.

1j

1k

1l

1m

1n 2j
760 TTN, 63:37 e.r.
610 TTN, 30:70 e.r.[b]

2k
700 TTN, 59:41 e.r.[b]
790 TTN, 41:59 e.r.[c]

2l
330 TTN
78:22 e.r.

2m
750 TTN
91:9 e.r.

2n[a]
474 TTN
68:32 e.r.

2a-ent 1a 2a (Z)-1o

2o (*E*)-1o

2o-*dia*

2o-dia (Z)-1o 2o 2o-dia (E)-1o 2o (Z)-1o

+

(E)-1o

2o 2o-dia

1a 2a
97% yield
97:3 e.r.

3a
71% yield
97:3 e.r.

3b
79% yield
97:3 e.r.

3c
63% yield
95:5 e.r.

linezolid (Zyvox) bioisostere

Steps 1104 to 1108 can be repeated, as desired, until an acceptable activity and selectivity is achieved (a) $^5$4 + 1a → $^6$g + 7 + $Br^-$ (b) $^6$g + $Br^-$ → $^6$6

1a-Z 1a-E

ΔG = −0.6 kcal/mol
ΔH = 0.0 kcal/mol

7-Z 7-E

ΔG = −0.4 kcal/mol
ΔH = −0.4 kcal/mol $^{5}$TS1-a
17.7
(5.1)

$^{5}$TS1-b
19.1
(6.9)

$^{5}$TS3-a
6.3
(−7.7)

$^{5}$TS3-b
7.7
(−5.8)

$^{5}$TS3-c
8.0
(−5.6)

SEQUENCE LISTING

```
Sequence total quantity: 4
SEQ ID NO: 1           moltype = AA  length = 1050
FEATURE                Location/Qualifiers
source                 1..1050
                       mol_type = protein
                       organism = Bacillus megaterium
SEQUENCE: 1
TIKEMPQPKT FGELKNLPLL NTDKPVQALM KIADELGEIF KFEAPGRVTR YLSSQRLIKE  60
ACDESRFDKN LSQALKFARD FTGDGLVTSW THEKNWKKAH NILLPSFSQQ AMKGYHAMMV  120
DIAVQLVQKW ERLNADEHIE VSEDMTRLTL DTIGLCGFNY RFNSFYRDQP HPFIISMVRA  180
FDEVMNKLQR ANPDDPAYDE NKRQFQEDIK VMNDLVDKII ADRKARGEQS DDLLTQMLNG  240
KDPETGEPLD DGNIRYQIIT FLQAGHEATS GLLSFALYFL VKNPHVLQKV AEEAARVLVD  300
PVPSYKQVKQ LKYVGMVLNE ALRLWPIAPA FSLYAKEDTV LGGEYPLEKG DEVMVLIPQL  360
HRDKTVWGDD VEEFRPERFE NPSAIPQHAF KPFGNGQRAS IGQQFALHEA TLVLGMMLKH  420
FDFEDHTNYE LDIKETLSLK PKGFVVKAKS KKIPLGGIPS PSTEQSAKKV RKKAENAHNT  480
PLLVLYGSNM GTAEGTARDL ADIAMSKGFA PQVATLDSHA GNLPREGAVL IVTASYNGHP  540
PDNAKQFVDW LDQASADEVK GVRYSVFGCG DKNWATTYQK VPAFIDETLA AKGAENIADR  600
GEADASDDFE GTYEEWREHM WSDVAAYFNL DIENSEDNKS TLSLQFVDSA ADMPLAKMHG  660
AFSTNVVASK ELQQPGSARS TRHLEIELPK EASYQEGDHL GVIPRNYEGI VNRVTARFGL  720
DASQQIRLEA EEEKLAHLPL AKTVSVEELL QYVELQDPVT RTQLRAMAAK TVCPPHKVEL  780
EALLEKQAYK EQVLAKRLTM LELLEKYPAC EMKFSEFIAL LPSIRPRYYS ISSSPRVDEK  840
QASITVSVVS GEAWSGYGEY KGIASNYLAE LQEGDTITCF ISTPQSEFTL PKDPETPLIM  900
VGPGTGVAPF RGFVQARKQL KEQGQSLGEA HLYFGCRSPH EDYLYQEELE NAQSEGIITL  960
HTAFSRMPNQ PKTYVQHVME QDGKKLIELL DQGAHFYICG DGSQMAPAVE ATLMKSYADV  1020
HQVSEADARL WLQQLEEKGR YAKDVWAGLE                                  1050

SEQ ID NO: 2           moltype = AA  length = 666
FEATURE                Location/Qualifiers
source                 1..666
                       mol_type = protein
                       organism = Bacillus megaterium
SEQUENCE: 2
TIKEMPQPKT FGELKNLPLL NTDKPVQALM KIADELGEIF KFEAPGRVTR YLSSQRLIKE  60
ACDESRFDKN LSQGLKFLRD FLGDGLATSW THEKNWKKAH NILLPSFSQQ AMKGYHAMMV  120
DIAVQLVQKW ERLNADEHIE VSEDMTRLTL DTIGLCGFNY RFNSFYRDQP HPFIISLVRA  180
VDEVMNKLQR ANPDDPAYDE NKRQFQEDIK VMNDLVDKII ADRKARGEQS DDLLTQMLNG  240
KDPETGEPLD DGNIRYQIIT FLWAGHEGTS GLLSFALYFL VKNPHVLQKV AEEAARVLVD  300
PVPSYKQVKQ LKYVGMVLNE ALRLWPCVPA FSLYAKEDTV LGGEYPLEKG DEVMVLIPQL  360
HRDKTVWGDD VEEFRPERFE NPSAIPQHAF KPFGNGQRAA IGQQFALHEA TLVLGMMLKH  420
FDFEDHTNYE LDIKETFQLK PKGFVVKAKS KKIPLGGIPS PSTEQSAKKV RKKAENAHNT  480
PLLVLYGSNM GTAEGTARDL ADIAMSKGFA PQVATLDSHA GNLPREGAVL IVTASYNGHP  540
PDNAKQFVDW LDQASADEVK GVRYSVFGCG DKNWATTYQK VPAFIDETLA AKGAENIADR  600
GEADASDDFE GTYEEWREHM WSDVAAYFNL DIENSEDNKS TLSLQFVDSA ADMPLAKMHG  660
AFSTLE                                                            666

SEQ ID NO: 3           moltype = AA  length = 1050
FEATURE                Location/Qualifiers
source                 1..1050
                       mol_type = protein
                       organism = Bacillus megaterium
SEQUENCE: 3
TIKEMPQPKT FGELKNLPLL NTDKPVQALM KIADELGEIF KFEAPGRVTR YLSSQRLIKE  60
ACDESRFDKN LSQALKFARD FTGDGLVTSW THEKNWKKAH NILLPSFSQQ AMKGYHAMMV  120
DIAVQLVQKW ERLNADEHIE VSEDMTRLTL DTIGLCGFNY RFNSFYRDQP HPFIISMVRA  180
FDEVMNKLQR ANPDDPAYDE NKRQFQEDIK VMNDLVDKII ADRKARGEQS DDLLTQMLNG  240
KDPETGEPLD DGNIRYQIIT FLQAGHAATS GLLSFALYFL VKNPHVLQKV AEEAARVLVD  300
PVPSYKQVKQ LKYVGMVLNE ALRLWPIAPA FSLYAKEDTV LGGEYPLEKG DEVMVLIPQL  360
```

-continued

```
HRDKTVWGDD VEEFRPERFE NPSAIPQHAF KPFGNGQRAS IGQQFALHEA TLVLGMMLKH  420
FDFEDHTNYE LDIKETIYLK PKGFVVKAKS KKIPLGGIPS PSTEQSAKKV RKKAENAHNT  480
PLLVLYGSNM GTAEGTARDL ADIAMSKGFA PQVATLDSHA GNLPREGAVL IVTASYNGHP  540
PDNAKQFVDW LDQASADEVK GVRYSVFGCG DKNWATTYQK VPAFIDETLA AKGAENIADR  600
GEADASDDFE GTYEEWREHM WSDVAAYFNL DIENSEDNKS TLSLQFVDSA ADMPLAKMHG  660
AFSTNVVASK ELQQPGSARS TRHLEIELPK EASYQEGDHL GVIPRNYEGI VNRVTARFGL  720
DASQQIRLEA EEEKLAHLPL AKTVSVEELL QYVELQDPVT RTQLRAMAAK TVCPPHKVEL  780
EALLEKQAYK EQVLAKRLTM LELLEKYPAC EMKFSEFIAL LPSIRPRYYS ISSSPRVDEK  840
QASITVSVVS GEAWSGYGEY KGIASNYLAE LQEGDTITCF ISTPQSEFTL PKDPETPLIM  900
VGPGTGVAPF RGFVQARKQL KEQGQSLGEA HLYFGCRSPH EDYLYQEELE NAQSEGIITL  960
HTAFSRMPNQ PKTYVQHVME QDGKKLIELL DQGAHFYICG DGSQMAPAVE ATLMKSYADV  1020
HQVSEADARL WLQQLEEKGR YAKDVWAGLE                                   1050

SEQ ID NO: 4           moltype = AA  length = 1050
FEATURE                Location/Qualifiers
source                 1..1050
                       mol_type = protein
                       organism = Bacillus megaterium
SEQUENCE: 4
TIKEMPQPKT FGELKNLPLL NTDKPVQALM KIADELGEIF KFEAPGRVTR YLSSQRLIKE  60
ACDESRFDKN LSQALKFARD FAGDGLVTSW THEKNWKKAH NILLPSFSQQ AMKGYHAMMV  120
DIAVQLVQKW ERLNADEHIE VSEDMTRLTL DTIGLCGFNY RFNSFYRDQP HPFIISMVRA  180
VDEVMNKLQR ANPDDPAYDE NKRQFQEDIK VMNDLVDKII ADRKARGEQS DDLLTQMLNG  240
KDPETGEPLD DGNIRYQIIT FLLAGHEGTS GLLSFALYFL VKNPHVLQKV AEEAARVLVD  300
PVPSYKQVKQ LKYVGMVLNE ALRLWPVAPT FSLYAKEDTV LGGEYPLEKG DEVMVLIPQL  360
HRDKTVWGDD VEEFRPERFE NPSAIPQHAF KPFGNGQRAS IGQQFALHEA TLVLGMMLKH  420
FDFEDHTNYE LDIKETFQLK PKGFVVKAKS KKIPLGGIPS PSTEQSAKKV RKKAENAHNT  480
PLLVLYGSNM GTAEGTARDL ADIAMSKGFA PQVATLDSHA GNLPREGAVL IVTASYNGHP  540
PDNAKQFVDW LDQASADEVK GVRYSVFGCG DKNWATTYQK VPAFIDETLA AKGAENIADR  600
GEADASDDFE GTYEEWREHM WSDVAAYFNL DIENSEDNKS TLSLQFVDSA ADMPLAKMHG  660
AFSTNVVASK ELQQPGSARS TRHLEIELPK EASYQEGDHL GVIPRNYEGI VNRVTARFGL  720
DASQQIRLEA EEEKLAHLPL AKTVSVEELL QYVELQDPVT RTQLRAMAAK TVCPPHKVEL  780
EALLEKQAYK EQVLAKRLTM LELLEKYPAC EMKFSEFIAL LPSIRPRYYS ISSSPRVDEK  840
QASITVSVVS GEAWSGYGEY KGIASNYLAE LQEGDTITCF ISTPQSEFTL PKDPETPLIM  900
VGPGTGVAPF RGFVQARKQL KEQGQSLGEA HLYFGCRSPH EDYLYQEELE NAQSEGIITL  960
HTAFSRMPNQ PKTYVQHVME QDGKKLIELL DQGAHFYICG DGSQMAPAVE ATLMKSYADV  1020
HQVSEADARL WLQQLEEKGR YAKDVWAGLE                                   1050
```

COMPOSITIONS, SYSTEMS AND METHODS FOR ATOM TRANSFER RADICAL ADDITION REACTION

CROSS REFERENCE TO RELATED APPLICATIONS

This application is a national stage of PCT Patent Application No. PCT/US2022/074439 entitled "Compositions, Systems and Methods for Atom Transfer Radical Addition Reaction" filed Aug. 2, 2022, which claims priority to U.S. Provisional Application Ser. No. 63/228,562, entitled "Compositions, Systems and Methods for Atom Transfer Radical Addition Reaction," filed Aug. 2, 2021, which is herein incorporated by reference in its entirety.

TECHNICAL FIELD

The disclosure is generally directed to compositions, systems, and methods for performing atom transfer radical addition (ATRA) or atom transfer radical cyclization (ATRC) reaction, and more specifically the disclosure includes description of modified enzymes for catalyzing stereoselective atom transfer radical addition.

SEQUENCE LISTING

This application hereby incorporates by reference the material of the electronic Sequence Listing filed concurrently herewith. The material in the electronic Sequence Listing is submitted as an XML (.xml) file entitled "07431PCT_SeqList_ST26.xml" created on Aug. 2, 2022, which has a file size of 8 KB, and is herein incorporated by reference in its entirety.

BACKGROUND

As nature's privileged catalysts, enzymes are well-known for their ability to exert exquisite control over the stereochemical outcome of chemical reactions. Over the past three decades, the advent of directed evolution has enabled the rapid development of customized enzymes to furnish excellent catalytic activity and stereoselectivity which surpass those of traditional small-molecule catalysts, thus highlighting the potential of biocatalysis to revolutionize the practice of asymmetric synthesis. The catalytic repertoire of enzymes has been mostly limited to reactions found in nature, posing constraints on the types of products available from enzyme catalysis. Furthermore, to date, a variety of catalysis modes discovered and optimized by synthetic chemists has not been able to be performed by natural enzymes. To merge the excellent tunability and stereocontrol of biocatalysts with the synthetic versatility of abiotic systems, the discovery and development of new-to-nature enzymatic activity are widely recognized as preeminent objectives at the interface of modern biocatalysis and organic synthesis.

SUMMARY OF THE DISCLOSURE

Compositions, systems, and methods for performing biocatalytic atom transfer radical addition chemistry are described. Modified metalloenzymes are utilized to perform enantioselective and/or diastereoselective atom transfer radical addition chemistry on a broad range of substrates. Various biological enzymes can be modified to perform stereoselective ATRA/ATRC chemistry, including (but not limited to) various metalloenzymes such as heme enzymes (e.g., cytochromes P450, cytochromes c, protoglobins, and myoglobins), non-heme Fe enzymes, and other Co- and Cu-dependent metalloenzymes. Further, several embodiments are directed to the ability of performing stereoselective ATRA reactions on substrates having an unsaturated carbon-carbon bond, in which an alkyl halide substrate is selectively transfer to the alkene/alkyne to form a further saturated alkyl halide product.

In an aspect, a method is for conducting a controlled atom transfer radical addition or atom transfer radical cyclization reaction catalyzed by an unnatural metalloenzyme. The method provides a first substrate comprising an alkyl halide moiety, an aryl halide moiety, or other alkyl or aryl radical precursor. The method provides a second substrate comprising an unsaturated carbon-carbon moiety. The method provides a metalloenzyme catalyst that exerts enantiocontrol or diastereocontrol over the first and the second substrates. The method combines the first substrate, the second substrate, and the metalloenzyme catalyst to react such that an atom transfer radical addition reaction or an atom transfer radical cyclization reaction occurs to afford a product wherein the alkyl group and the halogen atom of the alkyl halide moiety are installed across the unsaturated C—C bond of the unsaturated moiety with a desirable enantiomer or and diastereomer outcome.

In some implementations, the first and second substrates are within a single molecule.

In some implementations, the first and second substrates are in two different molecules.

In some implementation, the halide of the alkyl halide moiety or aryl halide moiety bromide or chloride.

In some implementations, the unsaturated carbon-carbon moiety is an alkene or an alkyne.

In some implementations, the metal cofactor is Fe(II)/Fe(III) redox couple.

In some implementations, the metalloenzyme catalyst is: $P450_{ATRAse1}$, $P450_{ATRAse2}$, $P450_{ATRAse3}$, $P450_{ATRAse4}$, or an earlier variant from the $P450_{ATRAse1}$, $P450_{ATRAse2}$, $P450_{ATRAse3}$, or $P450_{ATRAse4}$ evolutionary lineage.

In some implementations, a metalloenzyme catalyst comprises a modified *Bacillus megaterium* P450 (CYP102A1) having one or more of the following mutations: A82T, L181F, L181V, I263Q, I263L, E267A, A268G, H266T, T327I, P327C, T327V, A330T, S400A, L436T, L437I, L437F, T438Q or S438Y.

In some implementations, the modified P450 has one or more of the following mutations: A82T, L181F, I263Q, H266T, or T327I.

In some implementations, the modified P450 has the following mutations: A82T, L181F, I263Q, H266T, and T327I.

In some implementations, the modified P450 has a sequence comprising SEQ ID No. 1.

In some implementations, the modified P450 has one or more of the following mutations: L181V, P327C, S400A, L436T or T438Q.

In some implementations, the modified P450 has the following mutations: L181V, P327C, S400A, L436T and T438Q.

In some implementations, the modified P450 has a sequence comprising SEQ ID No. 2.

In some implementations, the modified P450 has one or more of the following mutations: A82T, L181F, I263Q, E267A, T327I, L437I or S438Y.

In some implementations, the modified P450 has the following mutations: A82T, L181F, I263Q, E267A, T327I, L437I and S438Y.

In some implementations, the modified P450 has a sequence comprising SEQ ID No. 3.

In some implementations, the modified P450 has one or more of the following mutations: A82T, L181V, 1263L, A268G, T327V, A330T, L437F or S438Q.

In some implementations, the modified P450 has the following mutations: A82T, L181V, 1263L, A268G, T327V, A330T, L437F and S438Q.

In some implementations, the modified P450 has a sequence comprising SEQ ID No. 4.

In some implementations, a nucleic acid comprises a sequence for encoding a modified *Bacillus megaterium* P450 (CYP102A1) having one or more of the following mutations: A82T, L181F, L181V, I263Q, 1263L, E267A, A268G, H266T, T327I, P327C, T327V, A330T, S400A, L436T, L437I, L437F, T438Q or S438Y.

In some implementations, the nucleic acid comprises a sequence for encoding the modified P450 having one or more of the following mutations: A82T, L181F, I263Q, H266T, or T327I.

In some implementations, the nucleic acid comprises a sequence for encoding the modified P450 having the following mutations: A82T, L181F, I263Q, H266T, and T327I.

In some implementations, the nucleic acid comprises a sequence for encoding the modified P450 having a sequence comprising SEQ ID No. 1.

In some implementations, the nucleic acid comprises a sequence for encoding the modified P450 having one or more of the following mutations: L181V, P327C, S400A, L436T or T438Q.

In some implementations, the nucleic acid comprises a sequence for encoding the modified P450 having the following mutations: L181V, P327C, S400A, L436T and T438Q.

In some implementations, the nucleic acid comprises a sequence for encoding the modified P450 having a sequence comprising SEQ ID No. 2.

In some implementations, the nucleic acid comprises a sequence for encoding the modified P450 having one or more of the following mutations: A82T, L181F, I263Q, E267A, T327I, L437I or S438Y.

In some implementations, the nucleic acid comprises a sequence for encoding the modified P450 having the following mutations: A82T, L181F, I263Q, E267A, T327I, L437I and S438Y.

In some implementations, the nucleic acid comprises a sequence for encoding the modified P450 having a sequence comprising SEQ ID No. 3.

In some implementations, the nucleic acid comprises a sequence for encoding the modified P450 having one or more of the following mutations: A82T, L181V, 1263L, A268G, T327V, A330T, L437F or S438Q.

In some implementations, the nucleic acid comprises a sequence for encoding the modified P450 having the following mutations: A82T, L181V, 1263L, A268G, T327V, A330T, L437F and S438Q.

In some implementations, the nucleic acid comprises a sequence for encoding the modified P450 having a sequence comprising SEQ ID No. 4.

BRIEF DESCRIPTION OF THE DRAWINGS

The description and claims will be more fully understood with reference to the following figures and data graphs, which are presented as exemplary embodiments and should not be construed as a complete recitation of the scope of the disclosure.

FIG. 2A provides the structure of exemplary substrate 1a, and its enantioselective atom transfer radical addition product 2a, while FIGS. 2B and 2C illustrate the directed evolution process of the metalloenzyme catalyst.

FIG. 4A provides a synthetic scheme for arriving at different enantiomers 2a and 2a-ent from a single starting substrate 1a, depending on the catalyst choice, while FIGS. 4B and 4C illustrate the directed evolution of the corresponding metalloenzyme catalysts.

FIGS. 5A and 6A provide synthetic schemes for arriving at different diastereomers 2o and 2o-dia from the corresponding regioisomers of starting substrate 1o, depending on the catalyst choice, while FIGS. 5B and 6B illustrate the directed evolution of the corresponding metalloenzyme catalysts.

DETAILED DESCRIPTION

Figure 1A:
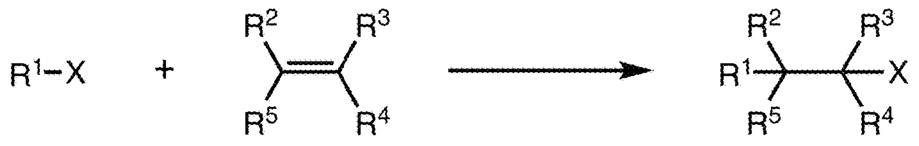
FIGS. 1A and 1B each provide a schematic illustration of biocatalytic enantio- and diastereoselective atom transfer radical addition (ATRA) or atom transfer radical cyclicalization (ATRC) reaction aided by engineered metalloenzymes in accordance with various embodiments.

Turning now to the drawings and data, compositions, systems and methods for performing stereoselective atom transfer radical addition (ATRA) reaction or atom transfer radical cyclization (ATRC) and applications thereof are described, in accordance with various embodiments. Several embodiments are directed to the use of modified biological enzymes to perform synthetic chemistry reactions with enantiocontrol and diastereocontrol. Particularly, many embodiments are directed to the use of a modified enzyme to perform an enantioselective ATRA or ATRC reaction. Various biological enzymes can be modified to perform stereoselective ATRA or ATRC chemistry, including (but not limited to) various metalloenzymes such as heme enzymes (e.g, cytochromes P450, cytochromes c, protoglobins, and myoglobins), non-heme Fe enzymes, and other Co- and Cu-dependent metalloenzymes. Further, several embodiments are directed to the ability of performing stereoselective ATRA or ATRC reactions on substrates having an alkene or alkyne, in which an alkyl halide substrate is selectively transfer to the alkene to form a more saturated alkyl halide product (FIG. 1A).

Due to the highly reactive nature of radical intermediates and the lack of synthetically realizable stereoinduction strategies, imposing enantiocontrol and diastereocontrol over free radical-mediated bond forming processes is a daunting challenge in asymmetric catalysis. As such, despite the widespread utility of atom transfer radical reactions in synthetic chemistry, the development of general methods for stereocontrolled ATRA or ATRC presents significant hurdles for conventional small-molecule catalysts. More specifically, due to the difficulty in maintaining tight association between a small molecule chiral catalyst and a radical intermediate, general catalytic strategies to exert enantiocontrol over, for example, a C—C bond forming radical addition step remains unavailable. Furthermore, imposing catalyst-controlled diastereoselectivity in, as another example, a subsequent halogen-rebound step is similarly challenging. Conventional catalytic strategies to accomplish excellent diastereocontrol over radical-mediated bond forming processes have long eluded synthetic chemists. As a result, radical-mediated reactions usually exhibit low diastereoselectivity under substrate control.

Natural enzymes such as radical SAM enzymes facilitate radical reactions with excellent chemoselectivity, regioselectivity and stereoselectivity. The vast majority of natural radical enzymes, however, display an extremely narrow substrate scope, and, thus, require extensive and often challenging engineering to afford generally useful catalysts for stereocontrolled radical chemistry. Nevertheless, it has been shown that various biological enzymes can be repurposed to catalyze unnatural radical reactions, leading to the development of novel biocatalytic methods, thereby allowing for a diverse array of easily available substrates to be converted with excellent operational simplicity.

Furthermore, metalloenzymes, such as heme-containing proteins can potentially provide opportunities for use as a general platform for asymmetric radical transformations. In general, heme chemistry has been proven useful, for example, in radical polymerizations, wherein polymer scientists have employed hemes to generate radical species for polymerization. In addition, metalloredox couples spanning a wide window of potentials, including Fe(II)/Fe(III), Co(I)/Co(II), and Cu(I)/Cu(II), are readily available in a variety of native metalloenzymes.

Through out the description, the terms ATRA and ATRC are used interchangeably. As would be understood in the art, the enzymes as described herein can be used in ATRA or ATRC reactions, depending the substrates utilized to perform the reaction.

Atom Transfer Radical Addition/Cyclization Chemistry

Several embodiments are directed to systems, compositions and methods for controlled formation and transformation of organic radicals catalyzed by modified metalloradical enzymes. In many embodiments, controlled formation and transformation of organic radicals is performed by an ATRA or ATRC reaction. In many embodiments, metalloenzyme catalysts comprise first-row transition-metal cofactors. Various organic radical manipulating methods of various embodiments utilize innate redox properties of the first-row transition-metal cofactors within metalloenzymes, and proceed via ground-state single electron transfer between the enzyme's metallocofactor and the substrate. In many embodiments, metalloenzyme catalysts are modified from natural analogs resulting in an intimate interaction between a desired substrate, including the corresponding reactive radical intermediate, and a metalloprotein scaffold of the metalloenzyme catalyst. In many embodiments, methods utilizing metalloenzyme catalysts provide enantiocontrol and diastereocontrol over the desired radical reactions, especially as compared to methods utilizing conventional small-molecule catalysts.

Figure 1B:
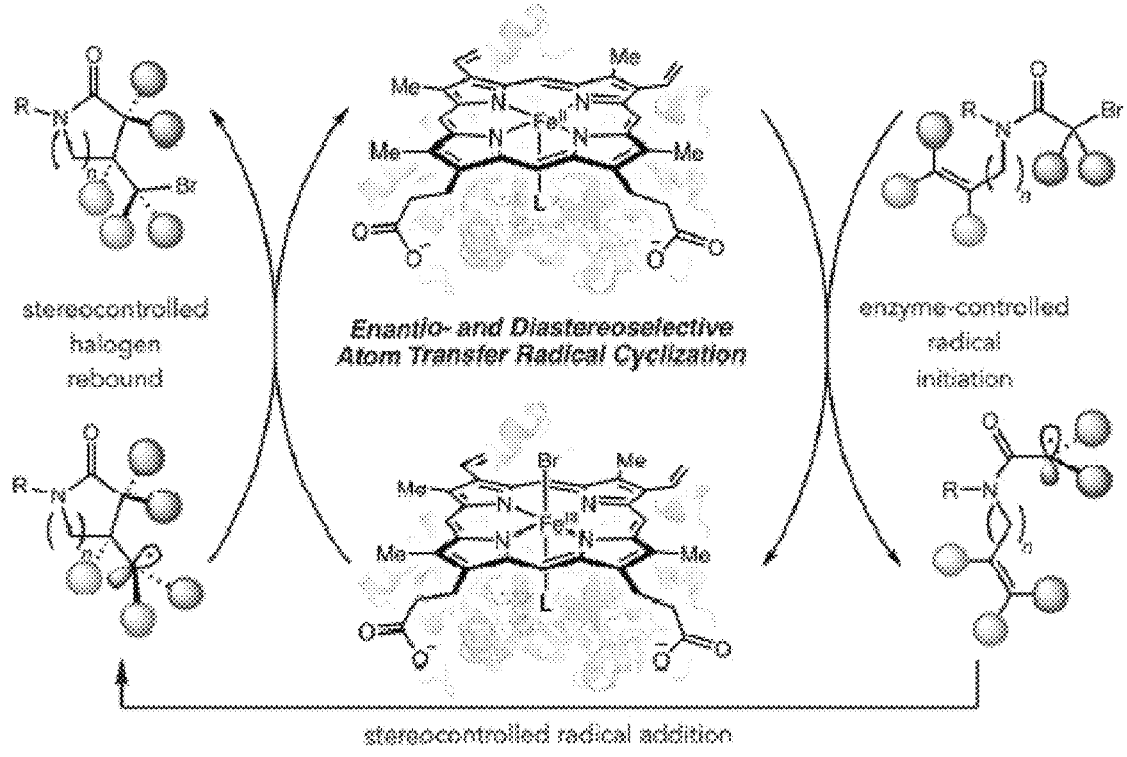

In many embodiments, metalloenzyme catalysts comprise a metal ion such as (for example) Fe(II)/Fe(III), Co(I)/Co(II), or Cu(I)/Cu(II). In some embodiments, a metalloenzyme catalyst comprise an iron ion supported by a heme scaffold. In embodiments utilizing an iron ion metalloenzyme catalyst, the metalloprotein catalyst in its ferrous state undergoes a single electron transfer with a first substrate comprising an organic halide, and produces a transient radical intermediate in the catalyst's active site (FIG. 1B). Rapid addition of the nascent radical species to a second substrate comprising an unsaturated system affords a new radical, which, subsequently, reacts with the ferric halide of the catalysts to furnish an ATRA product and regenerate the metalloenzyme catalyst. Accordingly, in many embodiments, various methods of ATRA reaction, wherein an alkyl group and a halogen atom are simultaneously installed across an unsaturated C—C bond (such as an alkene or an alkyne), generating enantiocontrolled and diastereocontrolled products. In many embodiments, protein modification methods described herein have resulted in development of several stereocomplementary catalysts, providing the ability to generate a variety of enantiodivergent and diastereodivergent ATRA products.

In many embodiments, the ATRA transformations between a radical precursor (including, but is not limited to, alkyl halides and aryl radical precursors) and an alkene/ alkyne afforded by the instant methods is most generally represented by the following scheme (see also FIG. 1A):

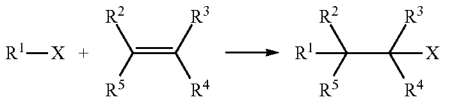

wherein, $R^1$ is an alkyl group; and $R^2$, $R^3$, $R^4$ and $R^5$ are each individually selected from the group consisting of: H, alkyl, aryl, acyl, CN, $NO_2$, R'R"N—, or R'O—, wherein, further, R' and R" are each an alkyl group, and wherein X is a halide. In some cases, the ATRA product undergoes elimination to provide the corresponding alkene product after the loss of HX. Although an alkene substrate is presented in the reaction drawing, it is understood that an alkyne substrate can be utilized as well.

Figure 2A:
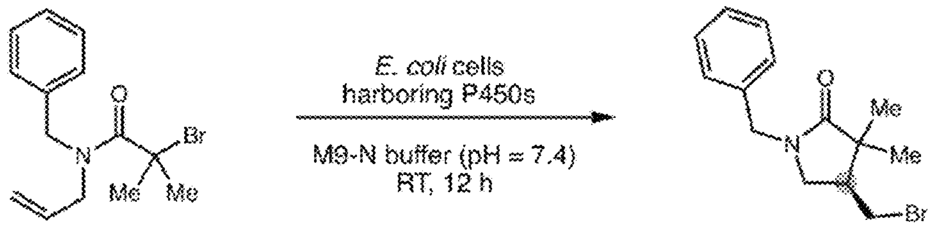
FIGS. 2A through 2C provide illustrations and data graphs of directed evolution of metalloenzyme catalysts for stereoselective ATRA reactions in accordance with various embodiments.
Figure 2B:
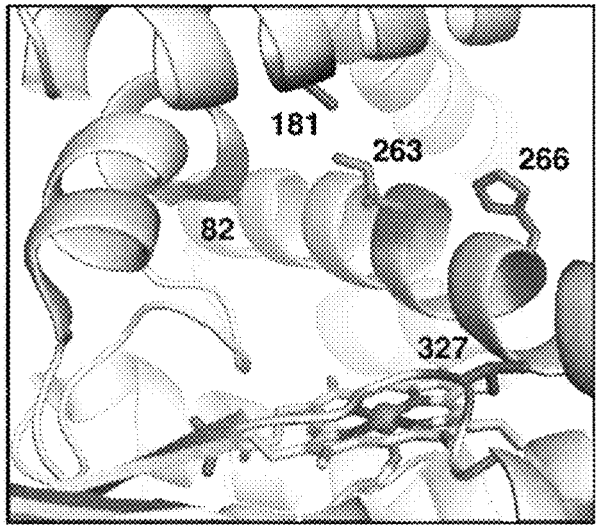
Figure 2C:
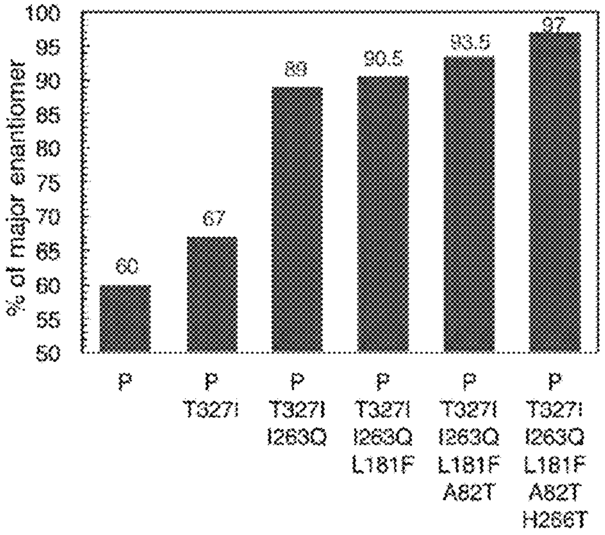
Figure 3:
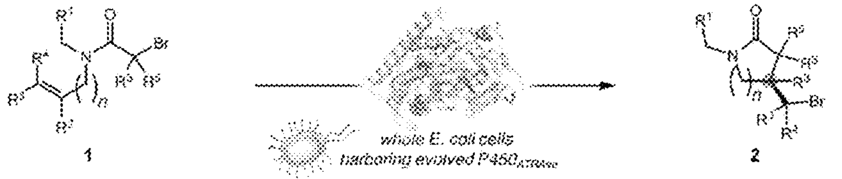
FIG. 3 provides molecular structures and reaction diagrams that illustrate the substrate scope of enantioselective atom transfer radical addition methods in accordance with various embodiments.
Figure 3:
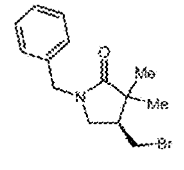
Figure 3:
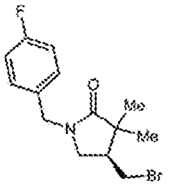
Figure 3:
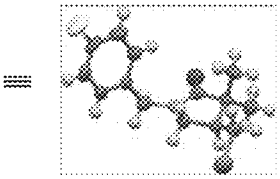
Figure 3:
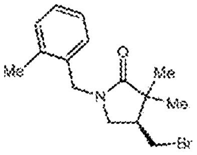
Figure 3:
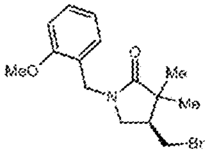
Figure 3:
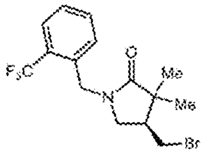
Figure 3:
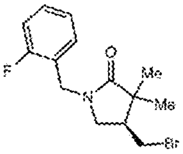
Figure 3:
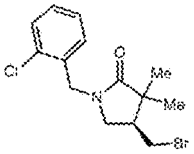
Figure 3:
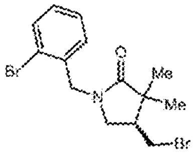
Figure 3:
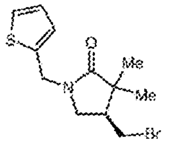
Figure 3:
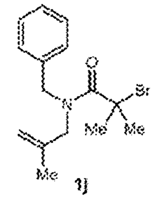
Figure 3:
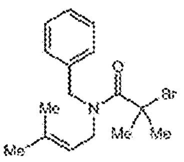
Figure 3:
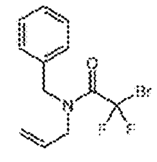
Figure 3:
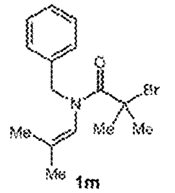
Figure 3:
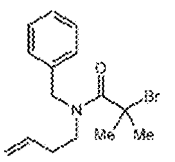
Figure 3:
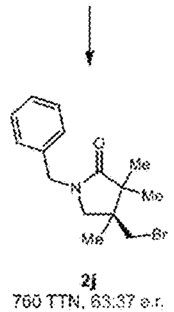
Figure 3:
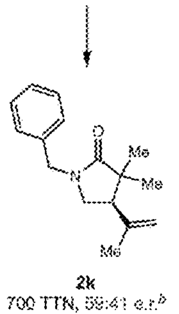
Figure 3:
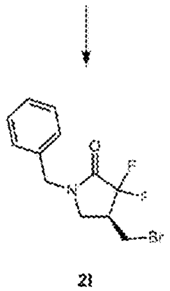
Figure 3:
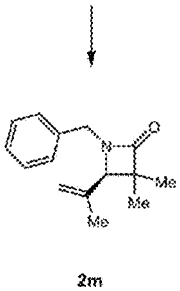
Figure 3:
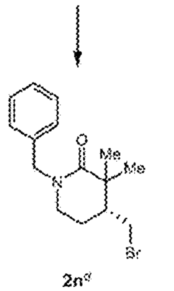

In some embodiments, an alkyl halide and unsaturated hydrocarbon moieties are combined in a single substrate to yield synthetic product with a cyclic entity, as illustrated, for example, in FIG. 2A. As such, FIG. 3 provides many examples to illustrate the scope of substrates for use with a particular metalloenzyme: cytochrome $P450_{ATRAse}$. Specifically, substrates having an alkyl halide moiety and an olefin can undergo an ATRA reaction to generate a ring closing within the substrate, resulting in a variety of optically active lactams. As seen from this exemplary illustration, in many embodiments, a wide range of functional groups, for example on the nitrogen substituent of examples 2a-2i, is readily tolerated by the instant methods, providing the corresponding γ-lactams in high yields (measured via the catalyst's total turnover number (TTN)) and enantioselectivity. Notably, halogen substituents (other than reactive site's halogen), are also compatible with biocatalytic ATRA methods, as illustrated by chloro-substituents and bromo-substituents in examples 2g and 2h, respectively, wherein such compatibility allows for valuable functional group handles for further derivatization. In some embodiments, substrates bear a heterocycle such as thiophene 2i. In some embodiments, the substrate's reactive olefin is an unsubstituted terminal alkene. In some embodiments, the substrate's reactive olefin bears one or more substitutions, such as, for example, illustrated by substituted olefins 1j, 1k, and 1m. In some embodiments the halide-bearing carbon of the substrate's alkyl halide moiety is further α,α-difluorinated, as illustrated by 1l. Notably, in many embodiments, the instant methods produce products bearing contiguous quaternary-quaternary stereocenters with stereocontrol, as illustrated by 2j. In some embodiments, with judicious substrate design, the instant methods also produce β- and δ-lactams, such as, for example, 2m and 2n, respectively, in an enantioselective fashion. As such, biocatalytic methods utilizing a modified metalloenzyme provide ability to produce a diverse array of enantioenriched lactams and other synthetic products.

Figure 4A:
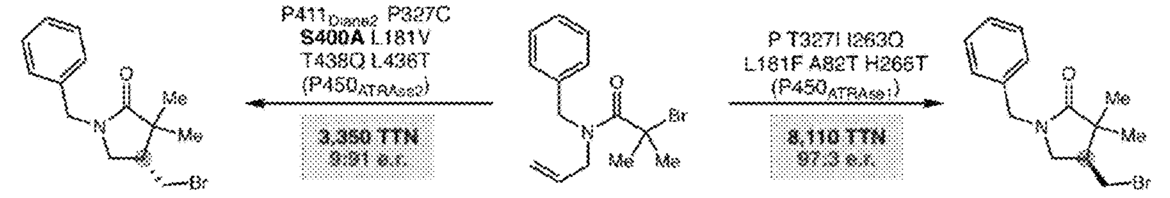
FIGS. 4A through 4C provide illustrations and data graphs of directed evolution of enantiodivergent ATRA metalloenzyme catalysts in accordance with various embodiments.
Figure 4B:
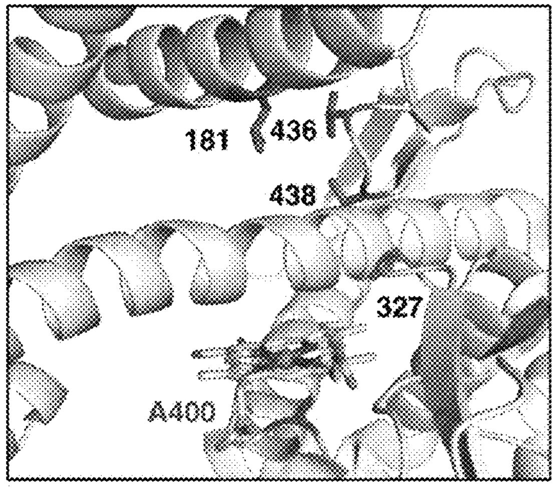
Figure 4C:
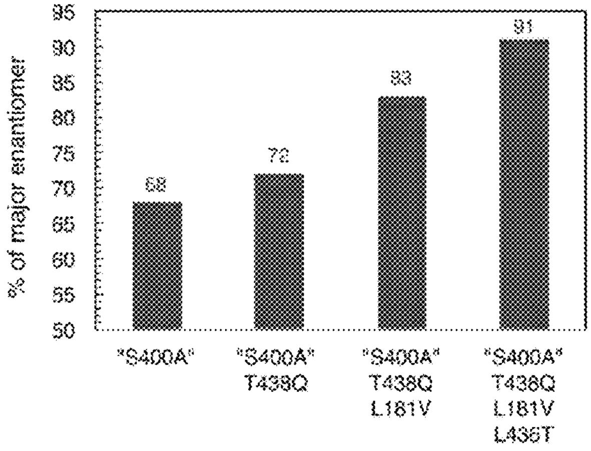

In some embodiments, various particular metalloenzyme catalysts are used to produce compounds with differing stereochemistries from the same substrate. For example, as shown in FIG. 4A, inverted enantiomers 2a and 2a-ent are obtained in excellent yield and corresponding enantiopurity from the same substrate 1a, depending on the choice of the metalloenzyme catalyst. As shown, metalloenzymes cytochrome $P450_{ATRAse1}$ and cytochrome $P450_{ATRAse2}$ each yield a unique enantiomeric product. Accordingly, various embodiments are directed to enantiocontrol of products from a single substrate utilizing a particular metalloenzyme catalyst.

Figure 5A:
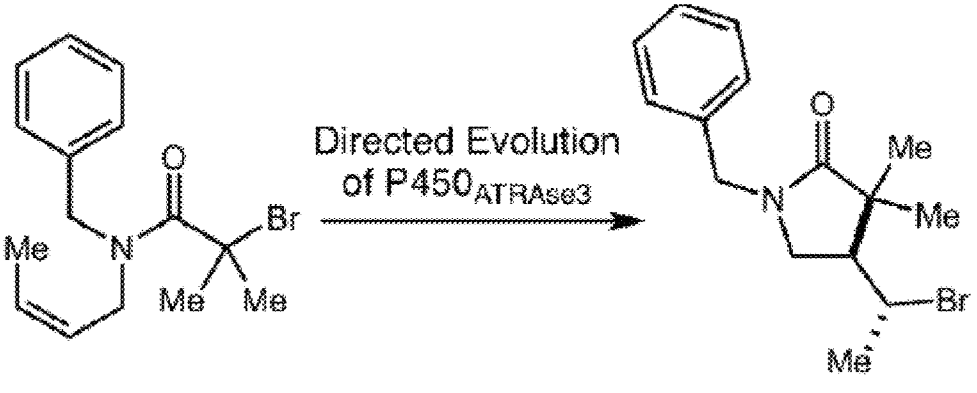
FIGS. 5A, 5B, 6A, and 6B provide illustrations and data graphs of directed evolution of diastereodivergent and diastereoconvergent ATRA metalloenzyme catalysts in accordance with various embodiments.
Figure 5B:
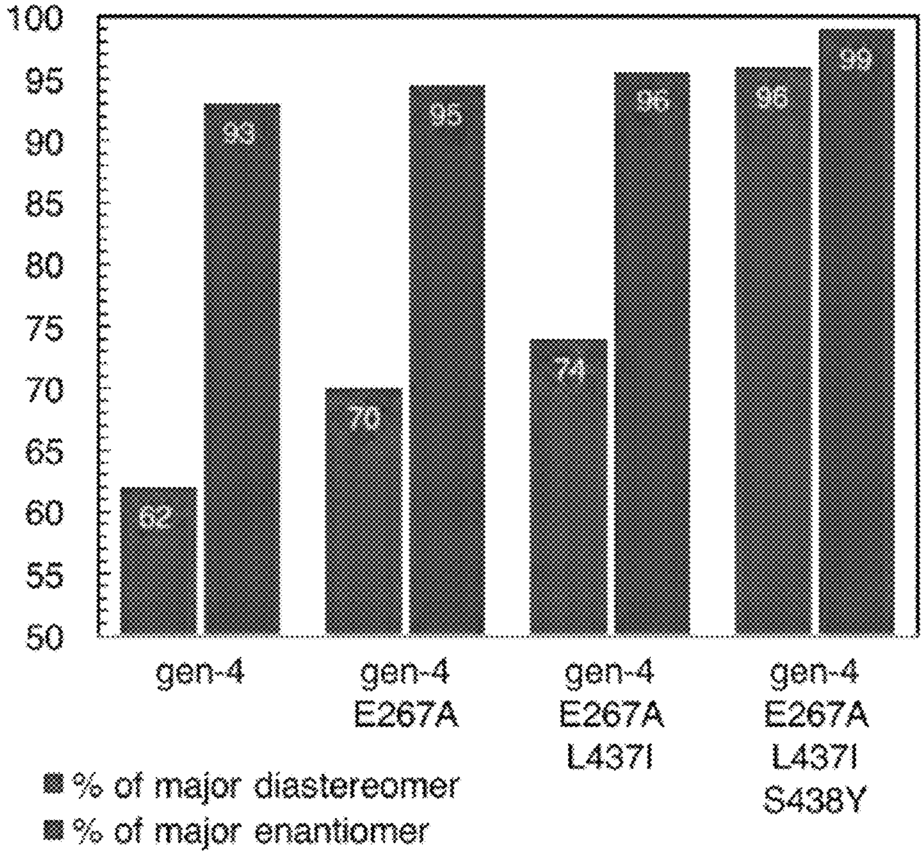
Figure 6A:
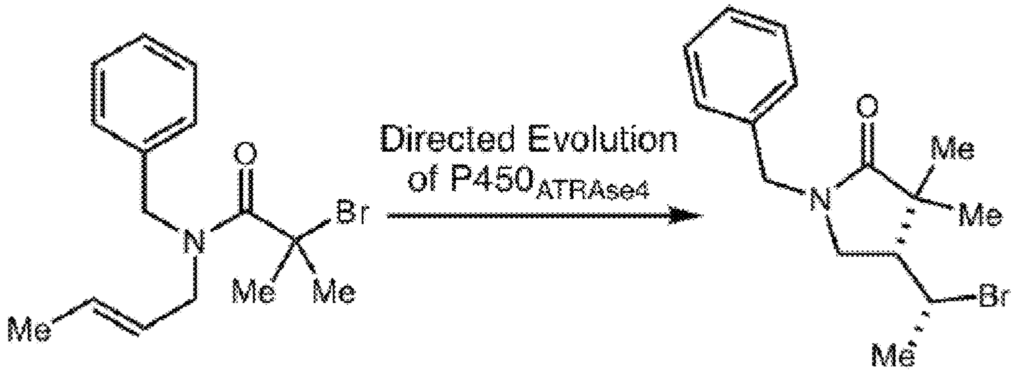
Figure 6B:
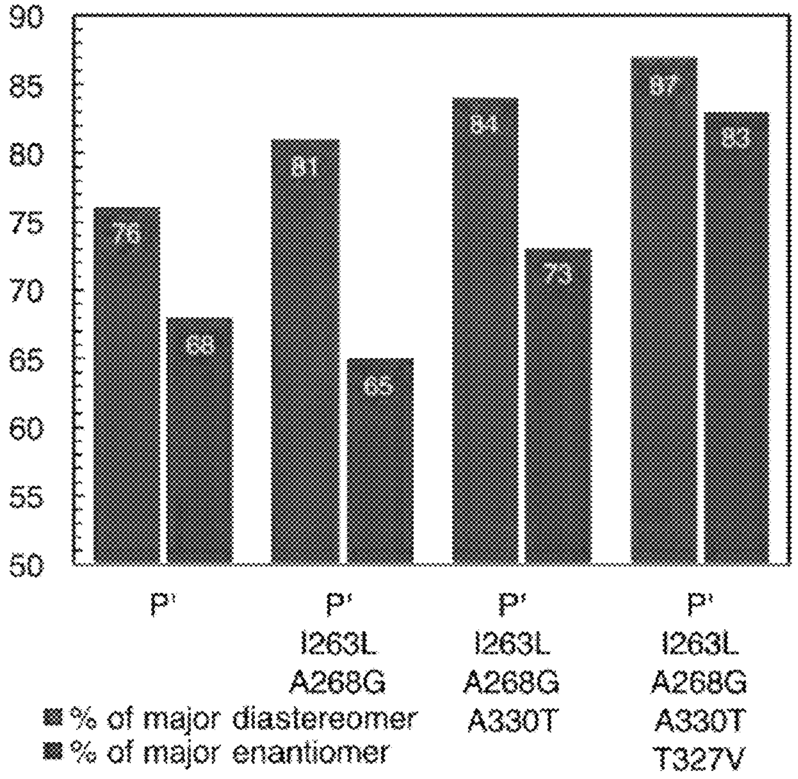
Figure 7:
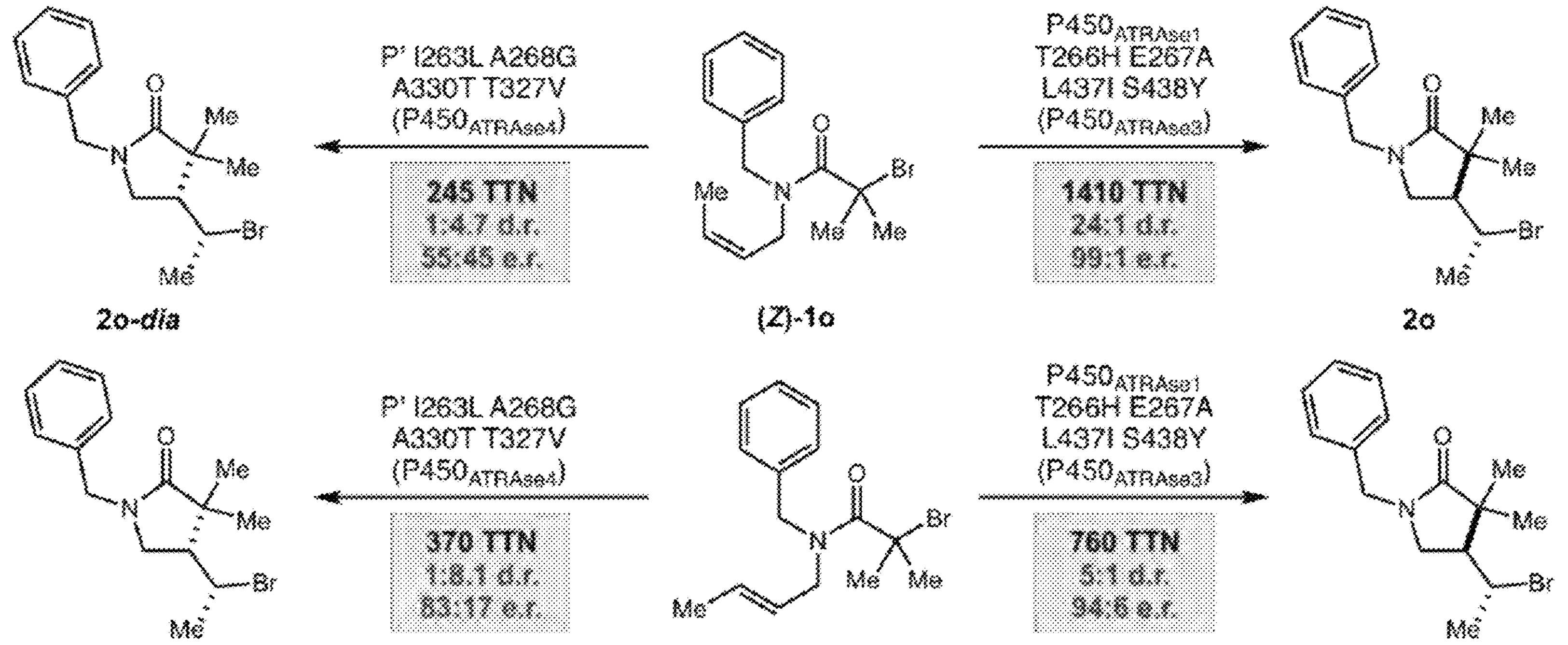
FIGS. 7 and 8 provide molecular structures and reaction diagrams that illustrate diastereocontrol capabilities of the ATRA methods in accordance with various embodiments.
Figure 8:
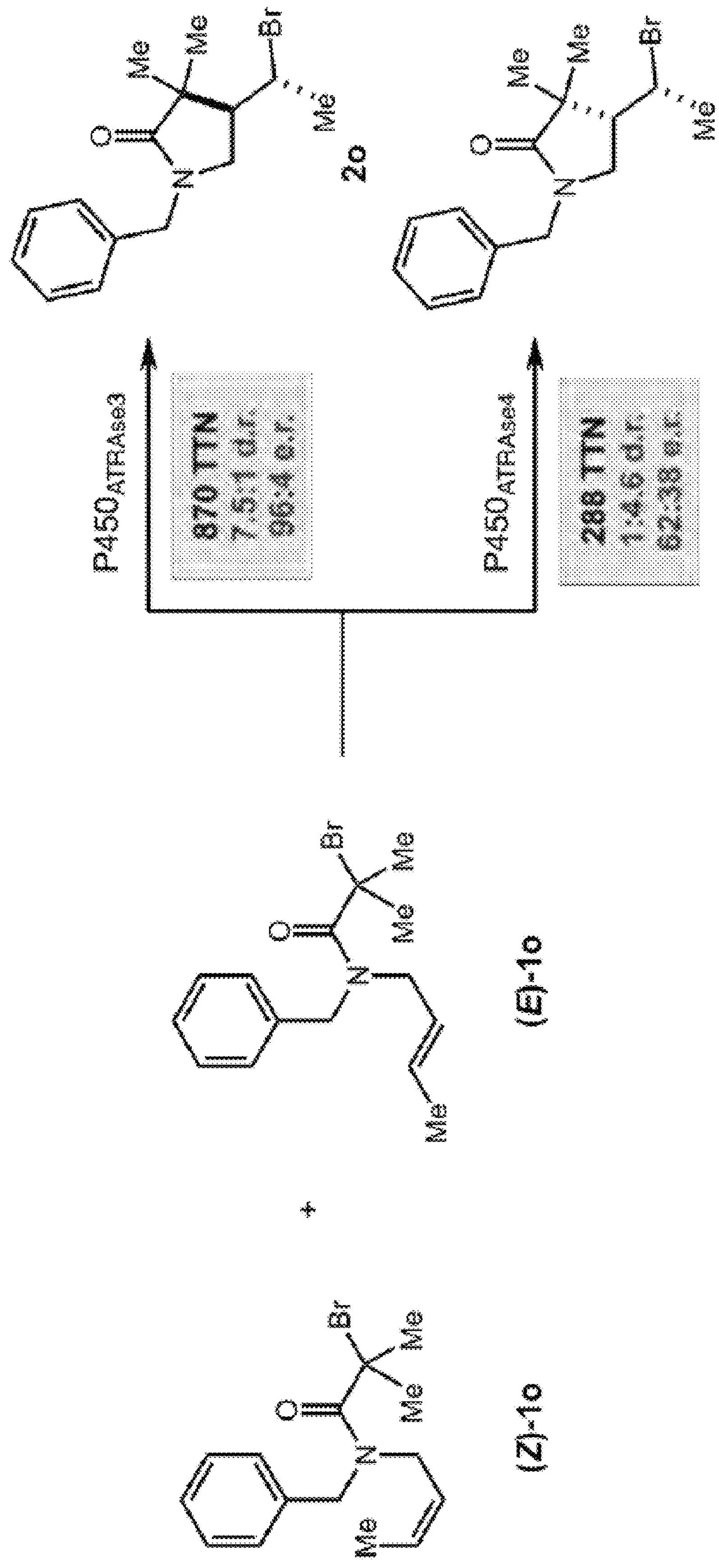

In various embodiments, easily accessible substrates and various particular metalloenzyme catalysts are utilized to obtain compounds with any desired diastereochemistry, based on the control of the relative stereochemistry in the C-halide bond forming halogen rebound event (FIG. 1A). For example, FIGS. 5A., 6A, 7, and 8 provide examples of diastereodivergent synthesis strategies for obtaining 2o or 2o-dia. For comparison, the use of conventional tris (2-pyridylmethyl) amine copper (I) catalyst for ATRA furnishes 2o and 2o-dia with much lower diastereoselectivity (1:1.6 and 2.1:1 d.r. from (E)- and (Z)-1g, respectively). Notably, substrates (E)- and (Z)-1g both afforded the same major diastereomer for both metalloenzyme catalyst choices (FIG. 7). Accordingly, the various methods employing particular metalloenzyme catalysts provide good to excellent diastereoselectivity and are used to obtain complex compounds with high stereopurity from easily accessible starting materials, including mixtures, as illustrated by FIG. 8, wherein 2o and 2o-dia are selectively obtained via proper metalloenzyme catalyst choice from a 1:1 mixture of (E)- and (Z)-1g.

Figure 9A:
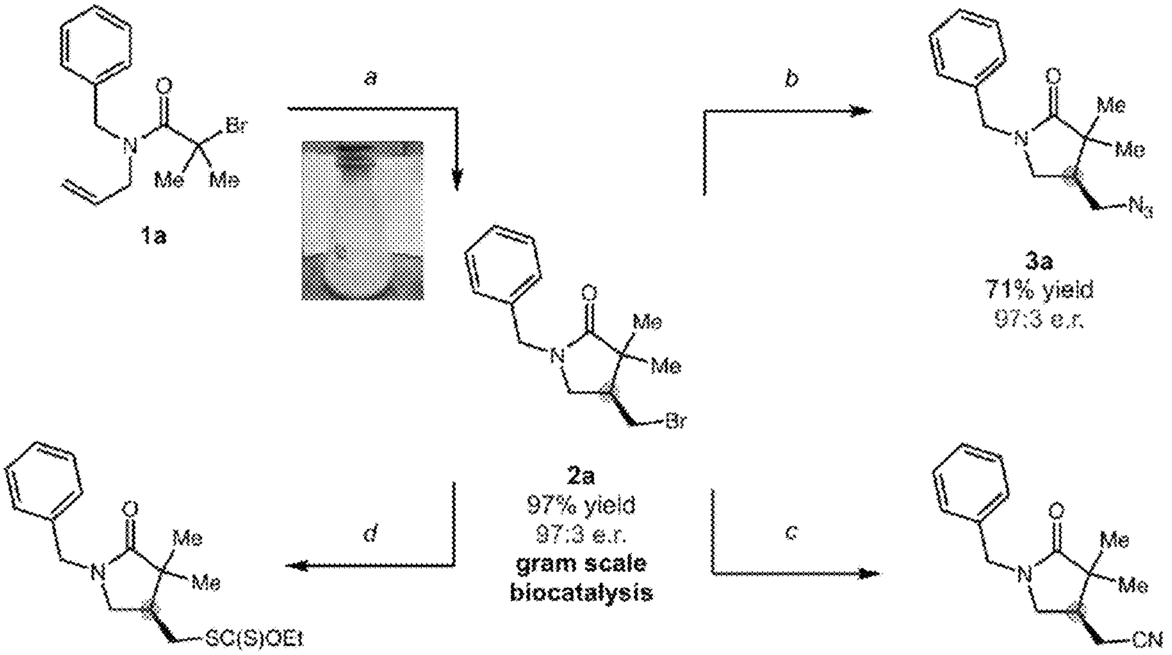
FIG. 9A provides molecular structures and reaction diagrams that illustrate gram-scale synthesis and further transformations of enantioenriched ATRA products in accordance with various embodiments.

In several embodiments, useful, practical, large scale synthesis of various products are produced. For example, FIG. 9A illustrates the whole-cell synthesis of 2a from 1a on a gram scale, utilizing a bacterial system expressing a particular modified metalloenzyme.

Figure 9B:
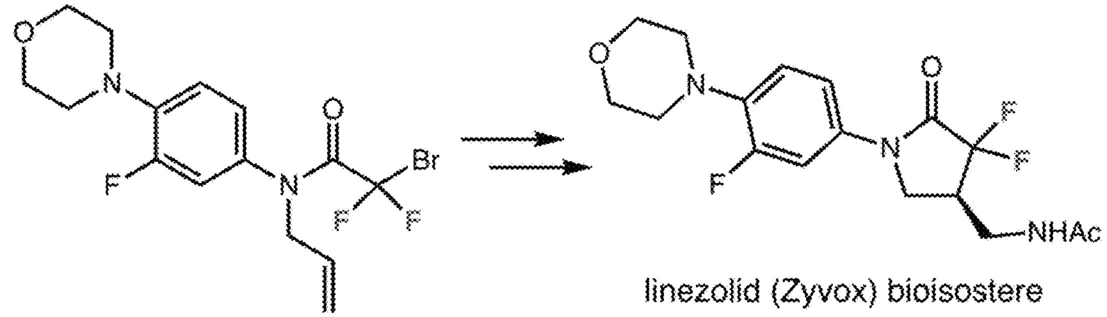
FIG. 9B provides molecular structures and reaction diagrams that schematically illustrate synthesis, including additional transformations, of an enantioenriched compound in accordance with various embodiments.

In many embodiments, the presence of a halide functional group in the enantioenriched ATRA products of the instant methods allows for a range of diversification reactions to be conveniently carried out post production. For example, as illustrated by FIG. 9A, $S_N2$-type nucleophilic substitution of 2a with a range of nucleophiles furnishes synthetically versatile compounds, such as azide (3a), cyanide (3b) and xanthate (3c), in good yields while maintaining the stereochemical purity. In turn, such derivatization reactions allow for a range of further formal enantioselective modifications, including, but not limited to: carbofunctionalization reactions, including carboazidation (for 3a), carbocyanation (for 3b), and carboxanthation (for 3c). As another example of utility of the instant methods, FIG. 9B schematically illustrates that complex (including stereochemically), medicinally-valuable compounds, such as linezolid (Zyvox) bioisostere, can be easily obtained via the instant methods from much simpler, achiral substrates in only few steps.

Figure 10:
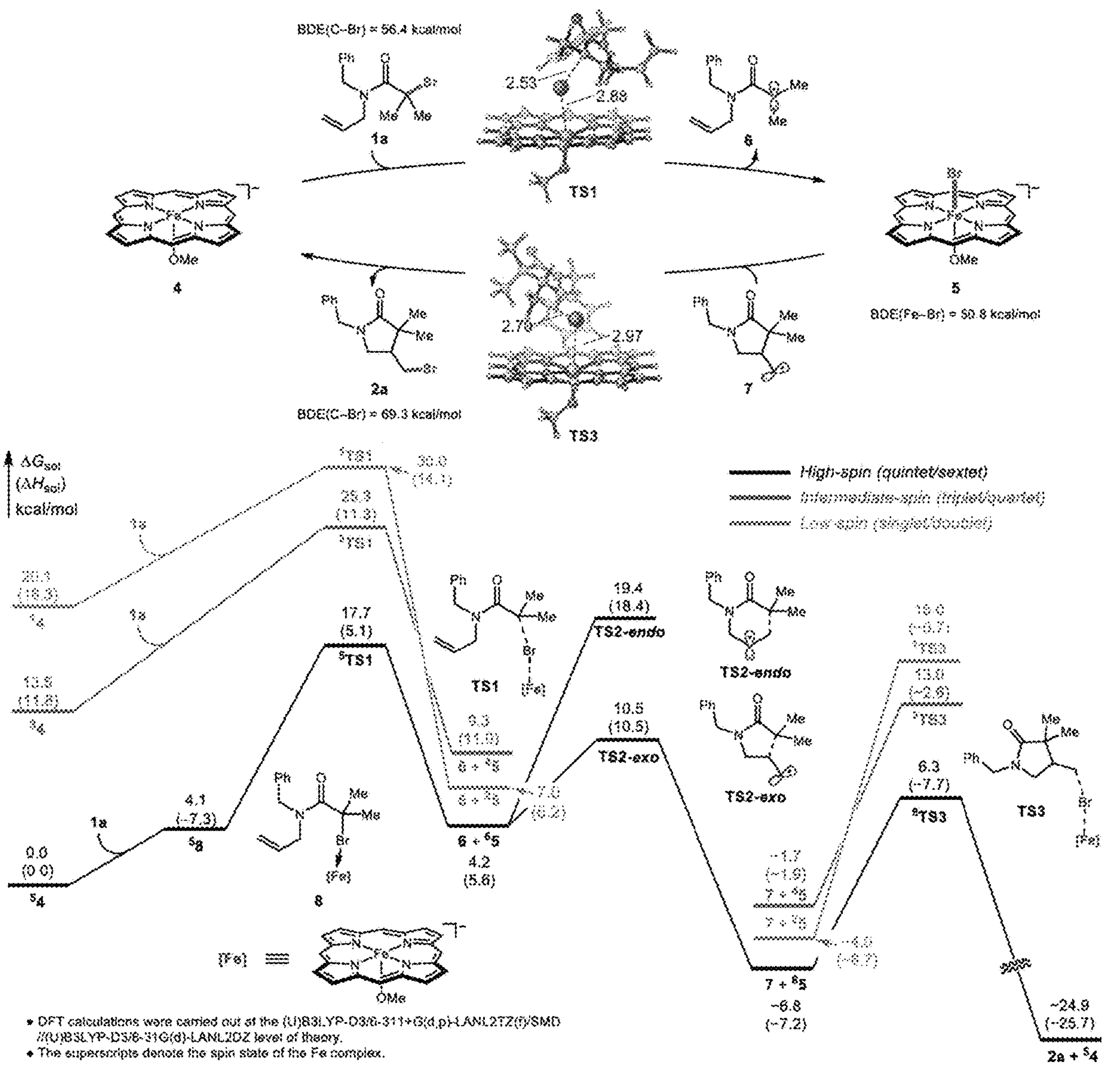
FIG. 10 provides molecular structures and reaction energy profile diagrams of ATRA methods using a model system for the axial serine-ligated Fe-porphyrin catalyst in accordance with various embodiments.

Not to be bound by any theory, FIG. 10 provides insights into the reaction mechanism of various methods employing metalloenzyme catalysts and the origin of the activity of the instant metalloenzyme catalysts in the ATRA reactions. More specifically, FIG. 10 illustrates density functional theory (DFT) calculations performed using a model system for a cytochrome P450 metalloenzyme catalyst. Based on a benchmark study of spin-state energies of 4 and 5 using the explicitly correlated local coupled-cluster method, PNO-LCCSD(T)-F12, as the reference, the (U)B3LYP-D3 functional is chosen in these calculations as it provided the best agreement with the PNO-LCCSD(T)-F12 results. DFT calculations show that the quintet Fe(II) catalyst ($^5$4) is 13.5 and 20.1 kcal/mol more stable than the triplet ($^3$4) and singlet ($^1$4), respectively. Similarly, the high-spin sextet ferric bromide intermediate ($^6$5) is 5.1 and 2.8 kcal/mol more stable than the quartet ($^4$5) and doublet ($^2$5), respectively. Thus, in the ATRA chemistry performed in accordance with various embodiments, the Fe-porphyrin catalyst remains high-spin throughout the catalytic cycle. This contrasts with the previously studied native oxene transfer and analogous nitrene transfer chemistry of P450 enzymes, each which involved spin crossover. Moreover, the Fe porphyrin system possesses several important features that make it an excellent choice for use with instant ATRA methods. First, with the model system, the radical initiation step (TS1) has a relatively low activation barrier (DG‡) of 17.7 kcal/mol and a free energy change (DG) of 4.2 kcal/mol. Considering that the enzyme environment will likely further facilitate this process by promoting substrate binding to form complex 8, this Fe-catalyzed radical initiation is expected to be highly kinetically facile. Second, after the selective 5-exo-trig cyclization (TS2-5 exo) to form the primary carbon radical 7, the bromine rebound step (TS3) is highly exergonic with a low activation barrier of 13.1 kcal/mol. The fast trapping of this newly formed carbon radical via bromine atom transfer renders the C—C bond formation step irreversible and enables kinetic control of reaction stereochemistry.

In addition, FIG. 10 illustrates further analyses to rationalize the high activity of the Fe system in promoting bromine atom transfer of the instant ATRA methods. To this end, the bond dissociation energy (BDE) of the Fe—Br linkage in the ferric bromide species (5) is 50.8 kcal/mol, which is slightly lower than that of the tertiary C($sp^3$)-Br bond in 1a (56.4 kcal/mol) and significantly lower than that of the primary C($sp^3$)-Br bond in 2a (69.3 kcal/mol). The BDE differences provide a strong thermodynamic driving force for bromine rebound to form 2a, while still permitting kinetically facile bromine abstraction from 1a. The rigid framework of the Fe porphyrin complex is another important factor facilitating the bromine atom transfer steps, because it lowers the distortion energy required for the Fe catalyst to reach the transition state structure. Additionally, the electron-rich nature of the Fe center allows for the facile single electron reduction of the substrate, as evidenced by the substantial electron transfer (0.44 $e^-$) from 4 to 1a in $^5$TS1. In fact, Marcus theory calculations indicate that the Fe porphyrin-based metalloenzyme catalyst is also highly effective in promoting the outer-sphere electron transfer, and the radical initiation step may involve a continuum of inner- and outer-sphere electron transfer mechanisms. Together, these results shed light on the mechanism of the instant atom transfer radical addition methods.

While specific examples of methods for performing atom transfer radical addition reactions with modified enzymes are described above, one of ordinary skill in the art can appreciate that various steps of the described methods can be performed in different orders and that certain steps may be optional according to some embodiments. Further, any appropriate reactant molecules and/or modified enzymes for performing an enantioselective and/or diastereoselective atom transfer radical addition reaction can be utilized. As such, it should be clear that the various steps of the method could be used as appropriate to the requirements of specific applications.

Compositions for Performing Atom Transfer Radical Addition Chemistry

Several embodiments are directed to compositions, especially modified enzymes, for performing ATRA chemistry. Furthermore, several embodiments are directed to methods for generating stereoselective enzymes via site-saturation mutagenesis and screening. Generally, a naturally occurring enzyme, such as a metalloenzyme, is modified at an amino acid residue (e.g., residues in the active site) to optimize the desired ATRA chemistry on a variety of substrates. Based on methods described herein, a number of modified enzymes for performing ATRA have been developed.

In accordance with various embodiments, modified enzymes for performing ATRA chemistry can be based on any appropriate enzyme, especially metalloproteins, and especially Fe-, Co-, and Cu-dependent proteins. In embodiments of Fe-dependent enzymes, either heme or non-heme proteins can be utilized. Examples of heme proteins include (but are not limited to) cytochromes P450, protoglobins, myoglobins, and cytochromes c. In some embodiments, a modified P450 enzyme is utilized. In some embodiments, a modified P450 enzyme includes a serine-ligated residue or lacks a coordinating axial residue (e.g., alanine is introduced to replace the original coordinating axial residue).

Particular embodiments of modified enzymes are directed towards modified *Bacillus megaterium* P450 (CYP102A1), which were developed via site-saturation mutagenesis on active site residues. It was found that the following mutations in P450 greatly enhanced enantioselective properties for performing ATRA: A82T, L181F, I263Q, H266T, and T327I. Accordingly, various embodiments are directed to P450 comprising one or more or all of these mutations. Modified P450 with these beneficial mutations (referred to as $P450_{ATRAse1}$ in the Example provided; SEQ ID No. 1), or earlier variants in the evolution series, had high enantioselectivity (97% product of major enantiomer) with a broad substrate scope.

It was further found that the following mutations in *Bacillus megaterium* P450 greatly enhanced enantioselective properties for performing ATRA: L181V, P327C, S400A, L436T and T438Q. Accordingly, various embodiments are directed to P450 comprising one or more or all of these mutations. Modified P450 with all five of these mutations (referred to as $P450_{ATRAse2}$ in the Example provided; SEQ ID No. 2), had high enantioselectivity (91% product of major enantiomer) with broad substrate scope. Notably, S400A disables serine ligation with the heme group.

It was further found that the following sets of mutations in *Bacillus megaterium* P450 greatly enhanced diastereoselective properties for performing ATRA in opposite chirality. To yield one of the diastereomers, the following mutations were found to have greatly enhanced diastereoselective properties: A82T, L181F, I263Q, E267A, T327I, L437I and S438Y. Accordingly, various embodiments are directed to P450 comprising one or more or all of these mutations. Modified P450 with all seven of these mutations (referred to as $P450_{ATRAse3}$in the Example provided; SEQ ID No. 3), had high diastereoselectivity (96% product of major diastereomer) and high enantioselectivity (99% product of major enantiomer) with broad substrate scope. To yield the other diastereomer, the following mutations were found to have greatly enhanced diastereoselective properties: A82T, L181V, 1263L, A268G, T327V, A330T, L437F and S438Q. Accordingly, various embodiments are directed to P450 comprising one or more or all of these mutations. Modified P450 with all seven of these mutations (referred to as $P450_{ATRAse4}$ in the Example provided; SEQ ID No. 4), had high diastereoselectivity (87% product of major diastereomer) and high enantioselectivity (99% product of major enantiomer) with broad substrate scope.

Figure 11:
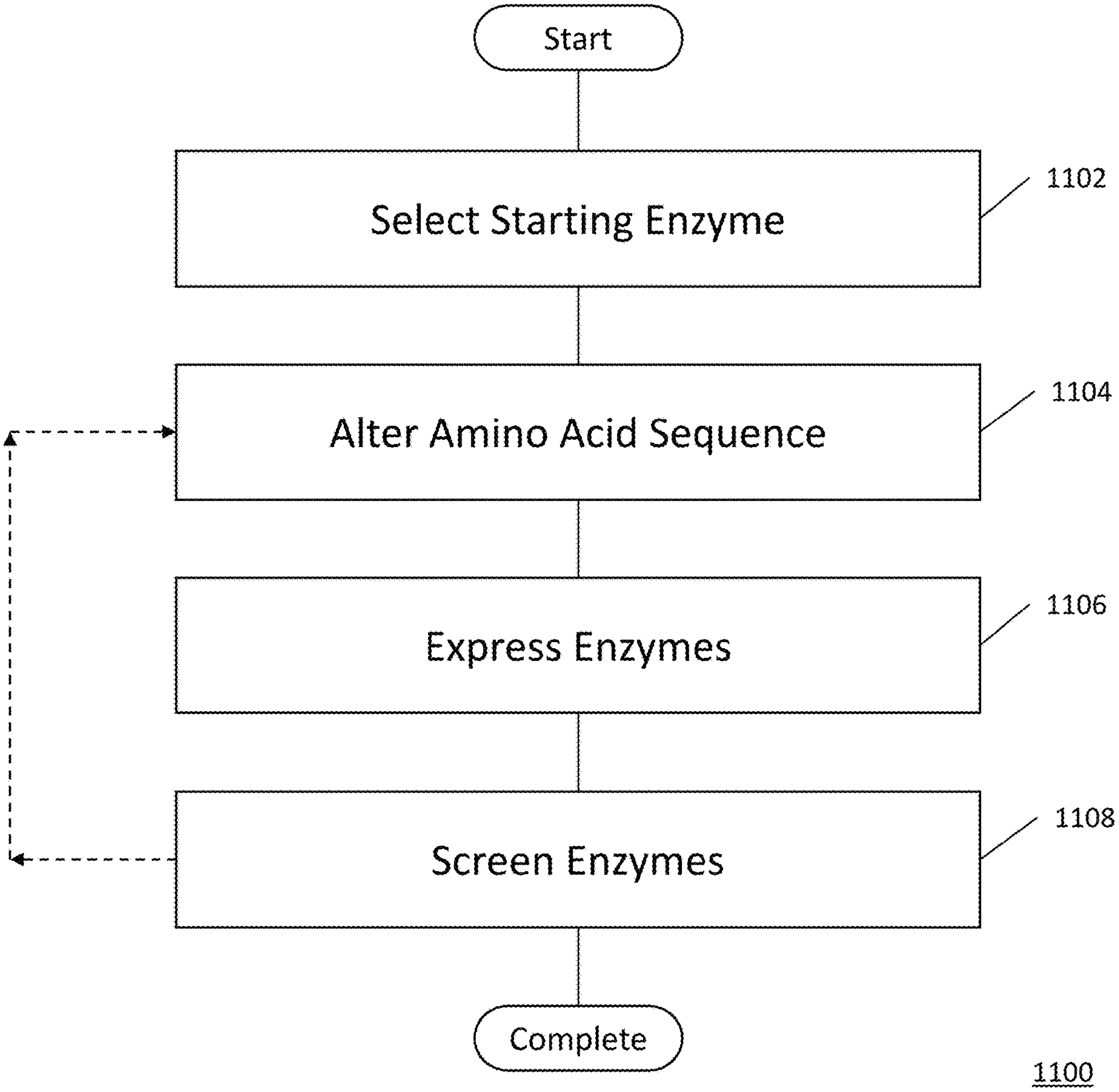
FIG. 11 provides a flow chart of a method to identify modified enzymes for performing ATRA chemistry in accordance with various embodiments.

Turning to FIG. 11, a method 1100 for generating enantioselective enzymes is illustrated. At 1102, various embodiments select a starting enzyme. The innate redox properties of first-row transition-metal cofactors in metalloenzymes may allow for controlled formation and transformation of organic radicals via ground-state single electron transfer between an enzyme's metallocofactor and a substrate; thus, in accordance with many embodiments, a metalloenzyme is selected as the starting enzyme. Various embodiments utilize a starting enzyme selected from heme and non-heme enzymes. Exemplary heme enzymes include (but are not limited to) cytochromes P450, cytochromes c, protoglobins, and myoglobins.

Many embodiments alter the amino acid sequence of the selected enzyme at 1104. In many embodiments, one or more amino acid residues in the active site of the selected enzyme are mutated to catalyze the enantioselective activity. Various methods are known in the art to alter amino acid sequences. Several embodiments utilize site-saturation mutagenesis (SSM) to alter amino acid residues. SSM is a method that systematically replaces wild type amino acids with all 19 non-wild type amino acids at selected positions (e.g., active site amino acid residues). Various embodiments alter the amino acid sequence by changing a coding sequence (e.g., DNA sequence) for the enzyme. Such amino acid changes are possible by making codon substitutions to the coding sequence for the enzyme. Certain embodiments utilize codon optimization of the coding sequence, or utilize codons that are efficient for translation for a particular organism (e.g., *E. coli*).

At 1106, further embodiments express the enzyme from an expression vector. In many embodiments, expression comprises transfecting or transforming a cell (e.g., bacterial cell, yeast cell, mammal cell, plant cell, etc.) or an organism with a sequence coding for the enzyme. In many embodiments, the coding sequence of the enzyme is assembled in an expression cassette, or construct, comprising one or more of a promoter, a terminator, a signaling peptide, an enhancer, a 5' untranslated region, a 3' untranslated region, a splice site, an origin of replication, and/or any other feature to aid in cloning, replication, transfection, or translation of the cassette or its contents.

At 1108, several embodiments screen the enzymes. Screening can include measuring one or more metrics that are preferable for an engineered enzyme. Various embodiments screen for one or more of enantioselective yield, enzymatic activity under specific conditions (e.g., temperature, pH, buffer, etc.), catalytic activity on specific reagents, or any other relevant metric for selecting an enzyme with preferable properties.

Many embodiments are directed to enzymes capable of enantioselectivity such as described herein. Some enzyme embodiments include SEQ ID NOs: 1-4. Further embodiments are directed to nucleic acid sequences (including, but not limited to, DNA and RNA) encoding for SEQ ID NOs: 1-4. Further embodiments are directed to cassettes or constructs used to replicate and/or express a coding sequence for an enantioselective enzyme. Many embodiments are directed to organisms transformed or transfected to express an enantioselective enzyme.

Figure 12:
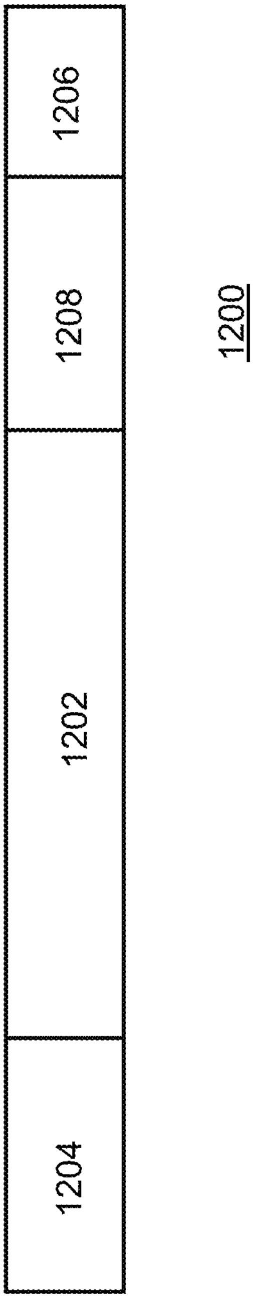
FIG. 12 provides a schematic of an expression cassette to express modified enzymes for performing ATRA chemistry in accordance with various embodiments.

Turning to FIG. 12, an exemplary expression cassette 1200 is illustrated in accordance with various embodiments. In many embodiments, expression cassette 1200 comprises a gene of interest 1202. In some embodiments, the gene of interest 1202 encodes for a functional peptide of interest, such as an enantioselective and/or diastereoselective enzyme. In certain embodiments, the gene of interest 1202 encodes a *Bacillus megaterium* P450 mutant protein described herein or a peptide selected from SEQ ID NOs: 1-4. In some embodiments, gene of interest 1202 includes one or more of a 5' untranslated region, a 3' untranslated region, an intron, or any other sequence typically located within a genic sequence and/or to enhance translation.

Additional embodiments are directed to transcript expression modifiers that are operatively linked to a gene of interest, including, 5' elements 1204 and/or 3' elements 1206, such as promoters, enhancers, terminators, etc., that assist with gene transcription and/or translation. Many types of promoters, enhancers, and terminators are known in the art, including constitutive and inducible promoters. Various embodiments include a constitutive promoter, including (but not limited to) T7 promoter, cauliflower mosaic virus 35S (CaMV 35S), cauliflower mosaic virus 19S (CaMV 19S), and/or any other constitutive promoter. Inducible promoters include (but are not limited to) galactose inducible promoters, copper inducible promoters, ethanol inducible promoters, and/or any other inducible promoter. Some embodiments include multiple expression modifiers, 5' elements 1204 and/or multiple 3' elements 1206 to further enhance gene transcription.

Further embodiments include one or more tags 1208, labels, or other peptides that can be used to identify, isolate, or export a protein of interest. For example, some cassettes include a His tag, a Myc tag, or other peptide tag that allows for identification or isolation of a protein of interest, while some embodiments include a signal peptide to transport the encoded peptide to a specific part of a cell or to export the encoded peptide outside of the cell.

Further embodiments of expression cassette 1200 include one or more of a splice site, an origin of replication, and/or any other feature to aid in cloning, replication, transfection of the expression cassette 1200. Additionally, while expression cassette 1200 is illustrated as a linear construct, several embodiments utilize a circularized construct (e.g., plasmid, fosmid, BAC).

Various embodiments include a cell transfected with an expression cassette, such as expression cassette 1200. In various embodiments, the cell is a plant cell, mammalian cell, fungal cell, bacterial cell, archaeal cell, etc. In some embodiments, a bacterial cell is used to express and secrete the protein of interest. Various embodiments utilize *E. coli* as the bacteria for expression.

EXEMPLARY DATA AND METHODS

The embodiments of the description will be better understood with experimental data. Attached herein is a description of methods and systems of exemplary modified enzymes and reactants for performing atom transfer radical addition chemistry. Validation results are also provided.

Experimental Methods

General

Unless otherwise noted, all chemicals and reagents were obtained from commercial suppliers (Sigma-Aldrich, VWR, Alfa Aesar, Combi-Blocks and Enamine) and used without further purification. Silica gel chromatography was carried out using AMD Silica Gel 60, 230-400 mesh. $^1H$, and $^{13}C$ NMR spectra were recorded on a Bruker 400 or 500 MHz instrument in CDCI3 or DMSO-$d_6$ and are referenced to residual protio solvent signals. $^{19}F$ NMR spectra (where applicable) were recorded on a Bruker 400 MHZ ($^1H$ decoupled) and are referenced to $CFCl_3$ as the external standard. Sonication on a small scale was performed using a BioLogics ultrasonic homogenizer (model 150VT) equipped with a stepped microtip. Sonication on a large scale was performed using a Branson Digital Sonifier 450 Ultrasonic Processor. All IR spectra were taken on a Thermo Scientific Nicolet iS5 spectrometer (iD5 ATR, diamond). High-resolution mass spectrometry data were obtained at the University of California Santa Barbara Mass Spectral Facility. High-resolution accurate mass (HRAM) ESI data was acquired using a Waters Micromass LCT Premier time-of-flight (TOF) mass spectrometer. Masses of positively charged ions were calibrated using methanol solutions of polyethylene glycol or polyethylene glycol monomethyl ether as an internal standard. Masses of negatively charged ions were calibrated using aqueous sodium formate or sodium/cesium iodide as an internal standard as appropriate. All samples were dissolved in methanol and were directly infused unless otherwise noted. Synthetic reactions were monitored by thin layer chromatography (TLC, Merck 60 gel plates) using a UV-lamp or an appropriate TLC stain for visualization.

*E. coli* cells were grown using Luria-Bertani medium (LB) or Hyperbroth (AthenaES) (HB) with 0.1 mg/mL ampicillin (LBamp or HBamp). Primer sequences for site-saturation mutagenesis or site-directed mutagenesis are provided below. T5 exonuclease, Phusion DNA polymerase, and Taq DNA ligase were purchased from New England Biolabs (NEB, Ipswich, MA). M9-N minimal medium (abbreviated as M9-N buffer; pH 7.4) was used as a buffering system for whole cells and lysates, unless otherwise specified. M9-N buffer was used without a nitrogen source; it contains 47.7 mM $Na_2HPO_4$, 22.0 mM $KH_2PO_4$, 8.6 mM NaCl, 2.0 mM $MgSO_4$, and 0.1 mM $CaCl_2$.

Chromatography

Analytical reversed-phase high-performance liquid chromatography (HPLC) was carried out using an Agilent 1200 series instrument and a Kromasil 100-5-C18 column (4.6×50 mm, 5 μm) with water and acetonitrile as the mobile phase. Analytical chiral HPLC was conducted using a Shimadzu i-series (66 MPa) instrument with hexanes and isopropanol as the mobile phase. Enantiomers were separated using one of the following chiral columns: Chiralpak IA (4.6 mm×25 cm, 5 micron), Chiralpak IB-N (4.6 mm×25 cm, 5 micron), Chiralpak IC (4.6 mm×25 cm, 5 micron), and Chiralpak IG (4.6 mm×25 cm, 5 micron). Gas chromatography (GC) analysis was carried out using a Shimadzu GC-2030 GC system equipped with an FID detector and with a J&W HP-5 ms column (30 m×0.25 mm, 0.25 μm film). Chiral GC was conducted using a Shimadzu GC-2030 GC system equipped with an FID detector and with an Agilent CycloSil-B column (30 m×0.32 mm, 0.25 μm film). Gas chromatography-mass spectrometry (GC-MS) analyses were carried out using a Shimadzu GCMS-QP2020NX system with a GC-2030 front end and a J&W HP-5 ms column (30 m×0.25 mm, 0.25 μm film).

Cloning and Site-Saturation Mutagenesis pET-22b(+) was used as the cloning and expression vector for metalloenzymes described in this study. Genes of metalloproteins were codon optimized using *E. coli* as the host organism and purchased as gBlocks from GeneralBio as plasmids in a desired vector. The genes of metalloenzymes used in this study were either cloned into pET-28a (+) between Nde I and Hind III (N-terminal 6× His tag) or cloned into pET-22b(+) between Nde I and Xho I (C-terminal 6× His tag). All the heme proteins described in this study cloned into pET-22b(+) between Nde I and Xho I with a C-terminal 6× His-tag. Site-saturation mutagenesis was performed using the “22c-trick” method. The PCR products were digested with Dpnl, gel purified, and ligated using a Gibson mix prepared from 5× isothermal (ISO) reaction buffer (25% PEG-8000, 500 mM Tris-HCl PH 7.5, 50 mM $MgCl_2$, 50 mM DTT, 1 mM each of the dNTPs, and 5 mM NAD), T5 exonuclease, Phusion DNA polymerase, and Taq DNA ligase. The ligation mixture was used directly to transform electrocompetent *E. coli* strain E. cloni BL21 (DE3) cells (Lucigen).

Expression of P450 Variants in 96-Well Plates

Single colonies from LBamp agar plates were picked using sterile toothpicks and cultured in deep-well 96-well plates containing LBamp (400 μL/well) at 37° C., 230 rpm shaking overnight. HBamp (900 μL/well) in a deep-well 96-well plate was then inoculated with an aliquot (100 μL/well) of these overnight cultures and allowed to shake for 2.5 h at 37° C. and 250 rpm. The plates were cooled on ice for 20 min and the cultures were induced with 0.5 mM isopropyl β-D-1-thiogalactopyranoside (IPTG) and 1.0 mM 5-aminolevulinic acid (final concentrations). Expression was conducted at 22° C., 220 rpm for 22 h.

Reaction Screening in 96-Well Plate Format

*E. coli* (*E. cloni* BL21 (DE3)) cells in deep-well 96-well plates were pelleted (3,000 g, 5 min, 4° C.) using an Eppendorf tabletop centrifuge 5910R and resuspended in M9-N buffer (345 μL/well) by gentle shaking using a Fisher Scientific microplate shaker (800 rpm, 3 min). 40 μL of D-glucose stock solution (500 mM in M9-N buffer) was added to each well using an Eppendorf Xplorer plus, 12-channel, 15-300 μL electronic pipette, and the 96-well plate was then transferred into a Coy anaerobic chamber. In the anaerobic chamber, 15 μL of the substrate stock solution (267 mM in EtOH) was added into each well using an Eppendorf Xplorer 12-channel pipette (15-300 μL). The plate was sealed with an aluminum foil and shaken in a Corning microplate shaker at room temperature and 680 rpm in the anaerobic chamber. After 7-18 h, the 96-well plate was taken out of the anaerobic chamber, the seal was removed and the analytical scale reactions were worked up following the appropriate method below.

Product formation screening and enantioselectivity screening using GC, GC-MS or normal phase HPLC. After 7-18 h, a solution of 1 mM 1,3,5-trimethoxybenzene (internal standard) in a mixed solvent system (hexanes/EtOAc=1:1, 600 μL) was added using an Eppendorf Xplorer plus, 12-channel, 50-1000 μL electronic pipette. The plate was tightly sealed with a reusable silicone mat, shaken vigorously for 30 times, and centrifuged (4500 g, 5 min) to completely separate the organic and the aqueous layers. The organic layers (350 μL/well) were transferred to 500 μL vial inserts using Eppendorf Xplorer, 12-channel, 15-300 μL electronic pipette. The inserts were then placed in 2 mL vials and analyzed by GC, GC-MS or normal phase HPLC. For normal phase HPLC analysis, chiral columns that are compatible with organic solvents, including IA, IB-N, IC and IG, were used.

Product formation screening using HPLC-MS. After 7-18 h, the reaction mixtures were quenched by the addition of EtOH or MeCN (800 μL/well). The plate containing the resulting mixture was tightly sealed with a reusable silicone mat, shaken vigorously and centrifuged (4500 g, 5 min) to pellet the cells. The supernatant (300 μL/well) was filtered through an AcroPrep 96-well filter plate (0.2 μm) into a shallow-well plate and analyzed by reverse-phase LCMS.

Expression of P450 Variants in 125 mL Erlenmeyer Flasks

*E. coli* (*E. cloni* BL21 (DE3)) cells carrying plasmid encoding the appropriate P450 variant were grown overnight in 4 mL LBamp. Preculture (3 mL) was used to inoculate 30 mL of HBamp in a 125 mL Erlenmeyer flask. This culture was incubated at 37° C., 230 rpm for 2.5 h. The culture was then cooled on ice for 20 min and induced with 0.5 mM IPTG and 1.0 mM 5-aminolevulinic acid (final concentrations). Expression was conducted at 22° C., 130 rpm, for 18 h. *E. coli* cells were then pelleted by centrifugation (3000 g, 5 min, 4° C.) using an Eppendorf 5910R tabletop centrifuge. Supernatant was removed and the resulting cell pellet was resuspended in M9-N buffer to OD600=1-60 (usually 5-30). An aliquot of this cell suspension (2 mL) was taken to determine protein concentration using the hemochrome assay after lysis by sonication. When applicable, the remaining cell suspension was further diluted with M9-N buffer to the OD600 used for the biotransformation and the concentration of P450 protein in the biotransformation was calculated accordingly.

Hemochrome Assay for the Determination of Protein Concentration

*E. coli* cells expressing heme protein resuspended in M9-N buffer were lysed by sonication using a BioLogics ultrasonic homogenizer (model 150VT) equipped with a stepped microtip (6 min in total, 1 sec on, 1 sec off, 40% amplitude); samples were submerged in wet ice for this process. The resulting lysed solution was centrifuged (15, 000 rpm, 10 min, 4° C.) using an Eppendorf microcentrifuge 5425R to remove the cell debris. The supernatant (clarified lysate) was separated from the pellet and kept on ice until use.

In a conical tube, a solution of 0.2 M NaOH, 40% (v/v) pyridine, 0.5 mM $K_3Fe(CN)_6$ was prepared (pyridine-NaOH—$K_3Fe(CN)_6$ solution). In another 1.5 mL centrifuge tube, a solution of 0.5 M $Na_2S_2O_4$ (sodium dithionite) was prepared in 0.1 M NaOH. 500 μL of clarified lysate in M9-N buffer and 500 μL of the pyridine-NaOH—$K_3Fe(CN)_6$ solution were transferred to a cuvette and carefully mixed. The UV-Vis spectrum of the oxidized $Fe^{III}$ state was recorded immediately. To the cuvette was then added 10 μL of the sodium dithionite solution. The cuvette was sealed with parafilm and the UV-Vis spectrum of the reduced $Fe^{II}$ state was recorded immediately. A cuvette containing 500 μL of M9-N, 100 μL 1 M NaOH, 200 μL pyridine, and 200 μL water (complete mixture without protein and $K_3Fe(CN)_6$) was used as a reference for all absorbance measurements. Concentrations of cytochromes P450 were determined using a published extinction coefficient for heme b, $\Sigma_{556(reduced)\text{-}540(oxidized)}$=23.98 $mM^{-1}cm^{-1}$.

Analytical Scale Biotransformations Using Whole *E. coli* Cells

Suspensions of *E. coli* (*E. cloni* BL21 (DE3)) cells expressing the appropriate heme protein variant in M9-N buffer (typically $OD_{600}$=30) were kept on ice. In another conical tube, a solution of D-glucose (500 mM in M9-N) was prepared. To a 2 mL vial were added the suspension of *E. coli* cells expressing P450 (typically $OD_{600}$=30, 345 μL) and D-glucose (40 μL of 500 mM stock solution in M9-N buffer). This 2 mL vial was then transferred into an anaerobic chamber, where the organic substrate (15 μL of 270 mM stock solution in EtOH) in succession. Final reaction volume was 400 μL; final concentrations were 10 mM substrate and 50 mM D-glucose. (Note: reaction performed with *E. coli* cells resuspended to $OD_{600}$=30 indicates that 345 μL of $OD_{600}$=30 cells were added, and likewise for other reaction $OD_{600}$ descriptions.) The vials were sealed and shaken at room temperature and 720 rpm for 7-18 h.

Preparative Scale Biotransformation Using Whole *E. coli* Cells

HBamp (1 L) in a 4 L flask was inoculated with an overnight culture (10 mL, 1% v/v, LBamp) of *E. coli* (*E. cloni* BL21 (DE3)) cells containing a pET-22b(+) plasmid encoding the desired enzyme variant. The cell culture was shaken at 37° C. and 230 rpm for ca. 3.5 h ($OD_{600}$=2-2.5). The culture was placed on ice for 30 min, and 5-aminolevulinic acid (1.0 mM final concentration) and IPTG (0.5 mM final concentration) were added. The culture was allowed to shake for 20 h at 22° C. and 150 rpm. Cells were pelleted by centrifugation (3,000 g, 5 min, 4° C.) using a Thermo Scientific Sorvall Lynx 6000 superspeed centrifuge, resuspended in M9-N buffer and adjusted to $OD_{600}$=30-40. An aliquot of cells (2 mL) was taken for the hemochrome assay to determine the concentration of the P450 enzyme. Cell suspensions in M9-N buffer were kept on ice until use. (Note: leaving the cell suspension at room temperature for an extended period of time will lead to significantly reduced enzyme activity.)

To a 1 L Erlenmeyer flask equipped with a screw cap were added a suspension of *E. coli* cells in M9-N buffer expressing the desired enzyme variant and a D-glucose stock solution. The flask was transferred to an anaerobic chamber, where a stock solution of the organic substrate (430 mM in EtOH) were added. The flask was capped, sealed with parafilm, taken out of the anaerobic chamber and allowed to shake in an Eppendorf Innova 44R shaker at room temperature at 200 rpm for 7-18 h.

The reaction mixture was extracted with EtOAc. The mixture was transferred to a 500 mL centrifugation bucket and centrifuged (15000 g, 30 min) using a Lynx 6000 superspeed centrifuge to separate the organic layer from the aqueous layer. The aqueous layer was extracted with EtOAc for an additional 2 cycles. Combined organic layers were dried over $MgSO_4$, concentrated in vacuo with the aid of a rotary evaporator and purified by column chromatography with the aid of a Biotage Isolera.

Normal Phase HPLC and GC Calibration Curve Development

Stock solutions of authentic products (100 mM in EtOAc) were prepared (at least 20 mg of sample was weighed to make a 100 mM stock solution in EtOAc). 1 L of extraction solvent with internal standard was freshly prepared (1 mmol (168 mg) of 1,3,5-trimethoxybenzene was added to a 1:1 mixture of hexanes and EtOAc (total volume=1 L)). (Note: Use a freshly prepared extraction mixture containing the internal standard due to the volatility of organic solvents. Use of aged extraction mixture will lead to inaccurate results.) To a microcentrifuge tube were added 400 μL of M9-N buffer, 3, 6, 12, 24, 48 μL product stock solution, respectively, and 600 μL extraction solvent. The mixture was vortexed (20 s for 3 times) and centrifuged (20,000 g, 5 min) to separate the organic and aqueous layers. The organic layer was transferred to a vial for normal phase HPLC and/or GC analysis. The calibration curves detailed below plot product concentration in mM (y-axis) against the ratio of the peak area of product to the peak area of internal standard from HPLC/GC analysis (x-axis). In the development of calibration curves, care was taken such that the calibration curve samples were prepared in a way similar to enzymatic samples. Similar practices are common in literature. Furthermore, assessment of the extraction efficiency of internal standard (1,3,5-trimethoxybenzene) revealed that this internal standard could be extracted into the organic phase almost quantitatively. In one example (2p), overlay of calibration curves prepared using this method and a method without taking distribution efficiency into consideration were given below, showing that the difference is minimal.

Protein Purification

*E. coli* (*E. cloni* BL21 (DE3)) cells carrying plasmid encoding a P450 variant were grown overnight in 10 mL LBamp (37° C., 250 rpm). HBamp (1 L) media in a 4 L flask was inoculated with 10 mL of the preculture and shaken for 3.5 h at 37° C. and 230 rpm. Cultures were cooled on ice (30 min) and induced with 0.5 mM IPTG and 1.0 mM 5-aminolevulinic acid (final concentrations). Expression was conducted at 22° C., 150 rpm, for 20 h. Cultures were then centrifuged (3,000 g, 10 min, 4° C.) using a Thermo Scientific Lynx 6000 superspeed centrifuge and the cell pellets were flash frozen with liquid nitrogen. For purification, frozen cells were resuspended in HisTrap buffer A (25 mM Tris, 100 mM NaCl, 20 mM imidazole, pH 7.5, 2-3 mL/g of cell wet weight) and lysed by sonication using a Branson Digital Sonifier 450 Ultrasonic Processor. To pellet cell debris, lysates were centrifuged using a Lynx 6000 superspeed centrifuge (15,000 g, 30 min, 4° C.). Alternatively, lysates were transferred to multiple 2 mL microcentrifuge tubes and centrifuged using an Eppendorf microcentrifuge (15,000 rpm, 30 min, 4° C.). The protein containing a C-terminal 6×His-tag was purified with a Ni-NTA column (5 mL HisTrap HP, GE Healthcare, Piscataway, NJ) using an AKTA Start protein purification system (GE healthcare). Proteins were eluted on a linear gradient from Histrap buffer A to His-trap buffer B (25 mM Tris, 500 mM imidazole, 100 mM NaCl, pH 7.5) over 10 column volumes (CV). Fractions containing the desired heme protein were combined, concentrated, and subjected to three exchanges of phosphate buffer (100 mM KPi, pH 8.0) using ultracentrifugal filters (10 kDa molecular weight cut-off, Amicon Ultra, Sigma Millipore) to remove excess salt and imidazole. Protein concentration was measured with Nanodrop and normalized to ca. 50 mg/mL. Typically, 1 L of $HB_{amp}$ expression culture provides 150 mg protein. Concentrated proteins were aliquoted, flash-frozen in liquid nitrogen and stored at −80° C. until further use. The concentration of the protein sample is determined by BCA assay using Thermo Scientific's protein BCA assay kit prior to use.

Analytical Scale Reactions Using Purified Metalloenzymes

Purified metalloprotein (ca. 50 mg/mL, 100 μL) was thawed and kept on ice. Stock solutions of the substrate (400 mM in EtOH), reductant (NADPH, $Na_2S_2O_4$, or ascorbic acid, 10-100 mM in an appropriate buffer) were prepared and transferred into an anaerobic chamber. Experiments with heme proteins were performed using 10 μM purified heme protein, 10 mM substrate, 1-10 mM reductant, in M9-N buffer (pH=7.4) or 0.1 M KPi buffer (pH=7.5) at room temperature under anaerobic conditions for 24 h. The total volume of analytical scale reactions using purified metalloenzymes is total volume=400 μL. The reaction mixture was then analyzed by chiral HPLC analysis for the determination of yield, TTN, and enantiomeric ratio (e.r.).

Evaluation of Metalloproteins for Stereocontrolled Atom Transfer Radical Cyclization At the outset of this study, a diverse collection of metalloenzymes were evaluated for this stereocontrolled atom transfer radical cyclization. While several enzymes displayed measurable initial activities, only two CYP102A1 variants in the metalloenzyme collection furnished measurable enantioselectivities. A subset of our heme protein screening results is summarized below.

TABLE 1

Select results on the evaluation of metalloproteins for stereocontrolled atom transfer radical cyclization

| metallo protein | UniProt ID | Organism | Annotation | Mutations | yield of 2a | ee of 2a |
|---|---|---|---|---|---|---|
| CYP102A1 F87A[a] | P14779 | *Bacillus megaterium* | cytochrome P450 naturally fused to its diflavin reductase ($P450_{BM3}$) | F87A | 4% | 0% |
| CYP119[a] | Q55080 | *Sulfolobus acidocaldarius* | cytochrome P450 | none | 5% | 0% |
| CYP101[a] | P00183 | *Pseudomonas putida* | cytochrome P450 ($P450_{cam}$) | none | 4% | 0% |
| Mb[a,b] | P02185 | *Physeter catodon* (sperm whale) | myoglobin | H64V V68A | 5%[a] (4%) [b] | 0% |
| Rma cyt c[a] | B3FQS5 | *Rhodothermus marinus* | cytochrome c | none | 4% | 0% |
| P411-CIS T438S (P) [a] | P14779 | *Bacillus megaterium* | axial serine-ligated cytochrome P450 | V78A, F87V, P142S, T175I, A184V, S226R, H236Q, E252G, T268A, A290V, L353V, I366V, C400S, T438S, E442K | 25% | 20% |
| $P411_{Diane2}$[a] | P14779 | *Bacillus megaterium* | axial serine-ligated cytochrome P450 | A74G, V78L, A82L, F87A, P142S, T175I, M177L, A184V, S226R, H236Q, E252G, I263W, | 20% | −26% |

TABLE 1-continued

| Select results on the evaluation of metalloproteins for stereocontrolled atom transfer radical cyclization | | | | | | |
|---|---|---|---|---|---|---|
| metallo protein | UniProt ID | Organism | Annotation | Mutations | yield of 2a | ee of 2a |
| | | | | T268G, A290V, T327P, A328V, L353V, I366V, C400S, T436L, L437F, E442K ΔFAD | | |
| PsEFE [b] | P32021 | *Pseudomonas savastanoi* | non-heme enzyme | none | 2% | 0% |
| EgtB [b] | G7CFI3 | *Mycobacterium thermoresistibile* | non-heme enzyme | none | 3% | 0% |
| BsQDO [b] | P42106 | *Bacillus subtilis* | non-heme enzyme | none | 1% | 0% |

[a]Activity screening was performed using whole-cell biocatalysts in a 96-well plate in a Coy anaerobic chamber. Heme proteins were induced with IPTG and ALA. Other metalloproteins were induced with IPTG. When induced with IPTG and ALA, control experiment using *E. coli* cells carrying an empty pET-22b(+) vector provided 3-4% yield. When induced with IPTG, control experiment using *E. coli* cells carrying an empty pET-22b(+) vector provided <1% yield.

[b] Activity screening was performed using purified protein catalysts (ca. 0.1 mol % catalyst loading) in a sealed 2.0 mL vial in a Coy anaerobic chamber. Control experiment under otherwise identical conditions in the absence of the metalloprotein catalyst provided no product.

Directed Evolution of $P450_{ATRAses}$

TABLE S2

Summary of directed evolution of $P450_{ATRAse1}$

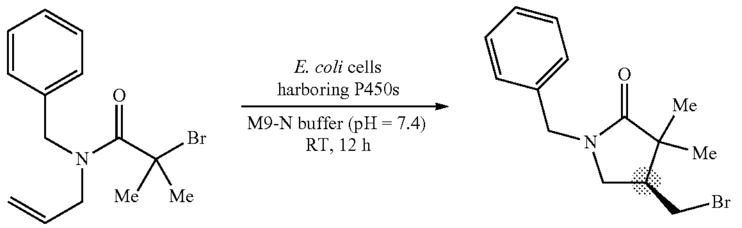

1a 2a

| Parent | Sites Targeted by SSM | Selection Criteria | Beneficial Mutation |
|---|---|---|---|
| P | V87X, T327X, S400X | enantioselectivity | T327I |
| P T327I | V87X, 1263X | enantioselectivity and activity | I263Q |
| P T327I I263Q | L181X, A82X, L437X | enantioselectivity | L181F A82T |
| P T327I I263Q L181F | A82X | enantioselectivity and activity | A82T |
| P T327I I263Q L181F A82T | H266X, E267X, M177X, A330X | enantioselectivity and activity | H266T E267A |
| P T327I I263Q L181F A82T H266T ($P450_{ATRCase1}$) | E267X | enantioselectivity | — |

TABLE 3

Directed evolution of P450 ATRCase1: enzyme activity and selectivity summary[a]

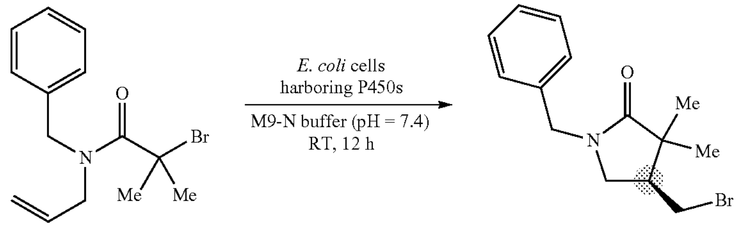

1a 2a

| Enzyme Variant | e.r. | TTN |
|---|---|---|
| P | 60:40 | 3010 ± 50 |
| P T327I | 67:33 | 1770 ± 80 |
| P T327I I263Q | 89:11 | 5320 ± 40 |
| P T327I I263Q L181F | 90.5:9.5 | 3790 ± 30 |
| P T327I I263Q L181F A82T | 93.5:6.5 | 3950 ± 70 |
| P T327I I263Q L181F A82T H266T ($P450_{ATRCase1}$) | 97:3 | 8110 ± 90 |

[a]All the whole-cell reactions were run in triplicates and averaged TTNs were described here.

TABLE 4

Atom transfer radical cyclization reactions using purified P450 variants

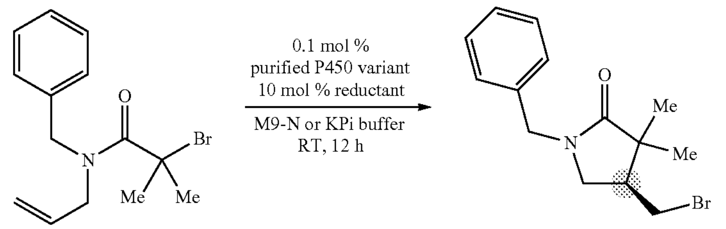

1a 2a

| Enzyme Variant | reductant | e.r. | yield (%) | TTN |
|---|---|---|---|---|
| P | NADPH | 60:40 | 31 ± 6 | 310 ± 60 |
| P T327I | NADPH | 67:33 | 5 ± 1 | 50 ± 10 |
| P T327I I263Q | NADPH | 89:11 | 45 ± 7 | 450 ± 70 |
| P T327I I263Q L181F | NADPH | 90.5:9.5 | 26 ± 1 | 260 ± 10 |
| P T327I I263Q L181F A82T | NADPH | 93.5:6.5 | 38 ± 1 | 380 ± 10 |
| P T327I I263Q L181F A82T H266T ($P450_{ATRAse1}$) | NADPH | 97:3 | 56 ± 6 | 560 ± 60 |
| P T327I I263Q L181F A82T H266T ($P450_{ATRAse1}$) | $Na_2S_2O_4$ | 97:3 | 47 ± 3 | 470 ± 30 |
| P T327I I263Q L181F A82T H266T ($P450_{ATRAse1}$) | ascorbic acid | 97:3 | 45 ± 3 | 450 ± 30 |

[a]All the in vitro reactions using purified P450 variants were run in duplicates and averaged yields and TTNs were described here.

As can be seen from Tables 3 and 4, for all the enzyme variants in the evolutionary lineage, the enantiomeric ratio (e.r.) for whole-cell reactions and purified enzyme reactions were identical, indicating minimal background reaction for *E. coli* cells overexpressing engineered $P450_{ATRAse}$. Additionally, the yields of purified enzyme reactions were found to be lower than whole-cell biotransformations, and the total turnover numbers (TTN) of purified enzyme reactions were an order of magnitude lower than those of whole-cell biotransformations. NADPH, $Na_2S_2O_4$ and ascorbic acid served as effective reducing reagent. In vitro reactions in the presence of NADPH provided slightly higher yields compared to those with $Na_2S_2O_4$ and ascorbic acid.

TABLE 5

| ATRA reaction with cofactor | | | |
|---|---|---|---|

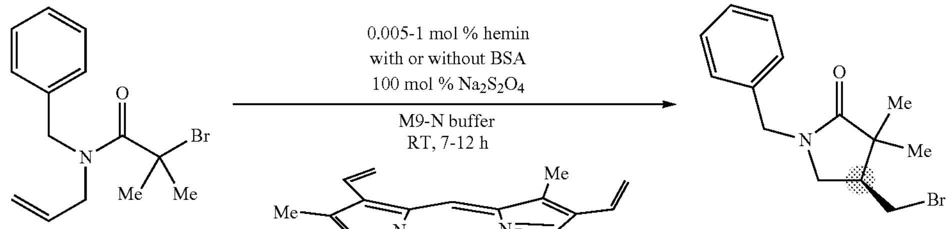

1a

2a

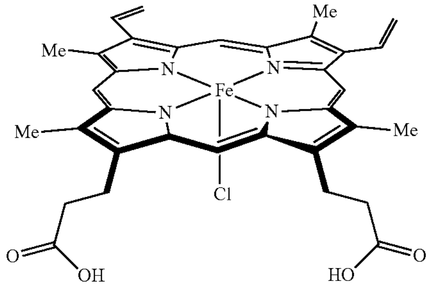

hemin

| hemin loading (mol %) | reaction time (h) | yield of 2a (%) | ee of 2a (%) |
|---|---|---|---|
| 1 | 7 | 17 ± 1 | 0 |
| 1 | 20 | 17 ± 1 | 0 |
| 0.1 | 7 | 9 ± 1 | 0 |
| 0.1 | 20 | 9 ± 1 | 0 |
| 0.005 | 7 | 1 ± 1 | 0 |
| 0.005 | 20 | 2 ± 1 | 0 |
| 1[a] | 20 | 17 ± 1 | 0 |

aHemin + bovine serum albumin (BSA).

Reduced hemin can catalyze this ATRC reaction with low levels of activity in a racemic fashion. Evolved enzymes $P450_{ATRAse}$ displayed a substantially higher activity under the same conditions. The use of hemin also led to the formation of a higher yield of undesired reduction product.

TABLE 6

Directed evolution of $P450_{ATRAse2}$: enzyme activity and selectivity summary[a]

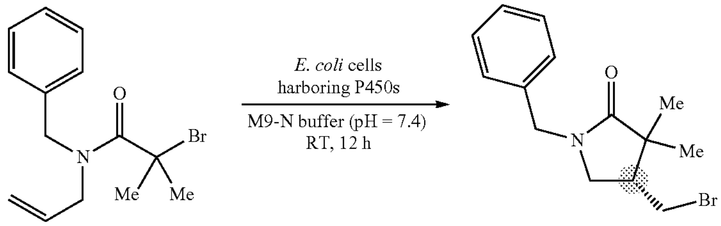

1a 2a-ent

| Enzyme Variant | e.r. | TTN |
|---|---|---|
| $P411_{Diane2}$ | 37:63 | 1250 ± 30 |
| $P411_{Diane2}$ P327C | 32:68 | 1160 ± 10 |
| $P411_{Diane2}$ P327C S400A | 32:68 | 1590 ± 20 |
| $P411_{Diane2}$ P327C S400A T438Q | 28:72 | 2240 ± 30 |
| $P411_{Diane2}$ P327C S400A T438Q L181V | 17:83 | 3400 ± 300 |
| $P411_{Diane2}$ P327C S400A T438Q L181V L436T ($P450_{ATRAse2}$) | 9:91 | 3350 ± 30 |

[a]All the whole-cell reactions were run in triplicates and averaged TTNs were described here.

TABLE 7

| Summary of directed evolution of $P450_{ATRAse2}$ | | | |
|---|---|---|---|
| Parent | Sites Targeted by SSM | Selection Criteria | Beneficial Mutation |
| $P411_{Diane2}$ | P327X, S400X | enantioselectivity | P437C S400A |
| $P411_{Diane2}$ P327C | W263X, S400X | activity | S400A |
| $P411_{Diane2}$ P327C S400A | T438X, L181X, L437X | enantioselectivity and activity | L181V T438Q |
| $P411_{Diane2}$ P327C S400A T438Q | L181X, L82X, A87X | enantioselectivity and activity | L181V |
| $P411_{Diane2}$ P327C S400A T438Q L181V | L436X, L78X | enantioselectivity and activity | L436T |
| $P411_{Diane2}$ P327C S400A L181V T438Q L436T ($P450_{ATRAse2}$) | — | — | — |

TABLE 8

Directed evolution of $P450_{ATRAse3}$: enzyme activity and selectivity summary[a]

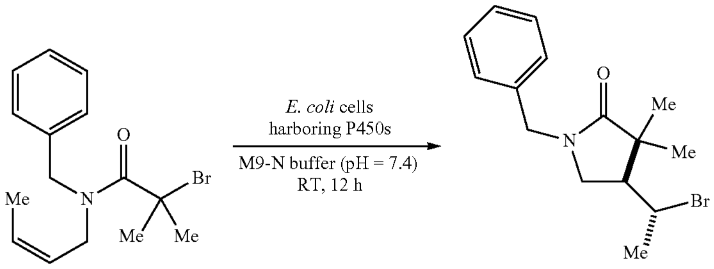

(Z)-1o 2o

| Enzyme Variant | d.r. | e.r. | TTN |
|---|---|---|---|
| P T327I I263Q L181F A82T (gen-4) | 62:38 | 93:7 | 1160 ± 10 |
| gen-4 E267A | 70:30 | 95:5 | 1040 ± 20 |
| gen-4 E267A L437I | 74:26 | 96:4 | 1220 ± 30 |
| gen-4 E267A L437I S438Y | 96:4 | 99:1 | 1410 ± 20 |

[a]All the whole-cell reactions were run in triplicates and averaged TTNs were described here.

TABLE 9

Directed evolution of $P450_{ATRAse4}$: enzyme activity and selectivity summary[a]

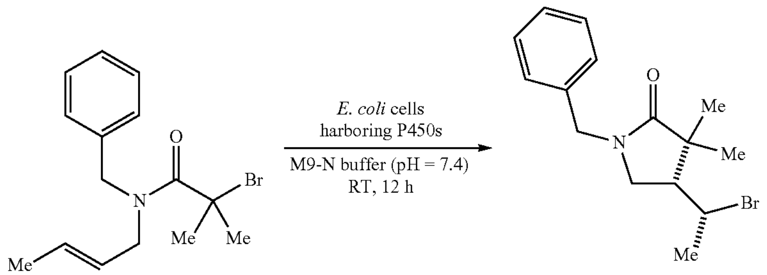

(E)-1o 2o-dia

| Enzyme Variant | d.r. | e.r. | TTN |
|---|---|---|---|
| P' | 76:34 | 68:32 | 550 ± 20 |
| P' I263L A268G | 81:19 | 65:35 | 610 ± 30 |
| P' I263L A268G A330T | 84:16 | 73:27 | 510 ± 30 |
| P' I263L A268G A330T T328V | 87:13 | 83:17 | 500 ± 30 |

[a]All the whole-cell reactions were run in triplicates and averaged TTNs were described here.

TABLE 10

High TTN experiments using whole *E. coli* cells harboring $P450_{ATRAse1}$

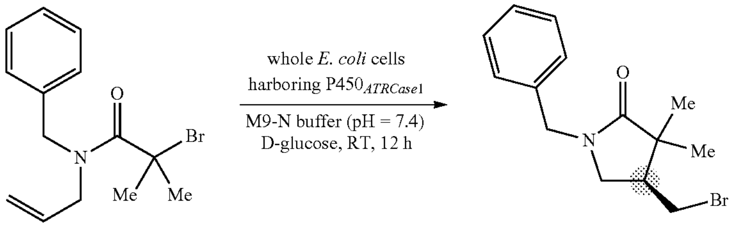

1a 2a

| OD600[a] | e.r. | TTN |
|---|---|---|
| 30 | 97:3 | 2090 ± 70 |
| 20 | 97:3 | 3180 ± 70 |
| 15 | 97:3 | 4480 ± 40 |
| 10 | 97:3 | 6800 ± 60 |
| 5 | 97:3 | 13200 ± 200 |
| 3 | 97:3 | 17990 ± 70 |
| 1 | 97:3 | 20000 ± 3000 |

[a]$OD_{600}$ here refers to the $OD_{600}$ of *E. coli* cell suspension used for catalysis and not the final $OD_{600}$ of whole-cell biotransformation. See General Procedure above for details.

TABLE 11

Whole-cell reactions carried out without using an anaerobic chamber

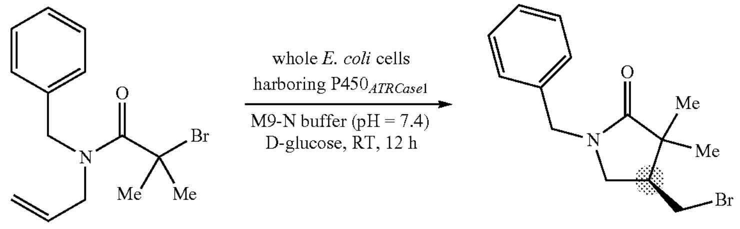

1a 2a

| Deviation from standard conditions | e.r. | yield |
|---|---|---|
| None (reaction was set up inside an anaerobic chamber) | 97:3 | 95% |
| Reaction was set up under air in a 2 mL vial. The vial remained uncapped throughout the course of the reaction. | 97:3 | 73% |
| Reaction was set up under air in a 2 mL vial. The vial was capped, but no special care was taken. | 97:3 | 95% |
| Reaction was set up under air in a 2 mL vial. 1 eq of $Na_2S_2O_4$ was added. | 97:3 | 90% |
| Reaction was set up under air in a 2 mL vial. 1 eq of ascorbic acid was added. | 97:3 | 95% |
| Reaction was set up under air in a 2 mL vial. Oxygen depleting system (glucose oxidase and catalase) was used. | 95:5 | 32% |

Diastereoselectivity in (TPMA) CuBr-Catalyzed ATRC of (E)- and (Z)-1o

Importantly prior work showed that bipy, TMEDA, PMDETA, TPMA, Mestren and other polydentate nitrogen ligand-based copper catalysts could affect ATRC reactions, although in a non-stereoselective fashion.

TABLE 12

Diastereoselectivity in (TPMA)CuBr-catalyzed ATRC reaction

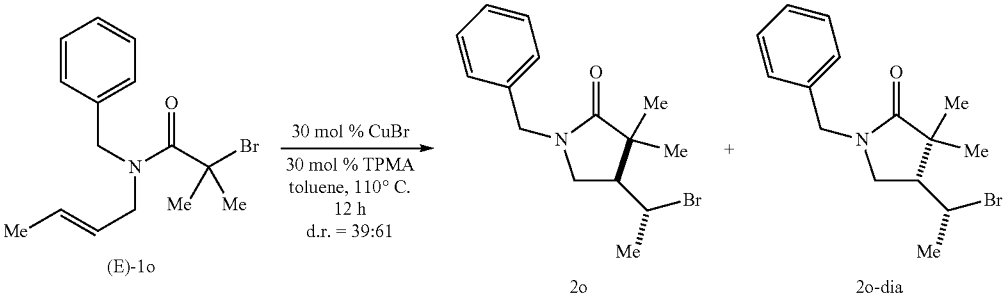 [SMILES: C/C=C/CN(Cc1ccccc1)C(=O)C(C)(C)Br ; C[C@@H](Br)[C@H]1CN(Cc2ccccc2)C(=O)C1(C)C ; C[C@@H](Br)[C@@H]1CN(Cc2ccccc2)C(=O)C1(C)C]

(E)-1o 2o 2o-dia

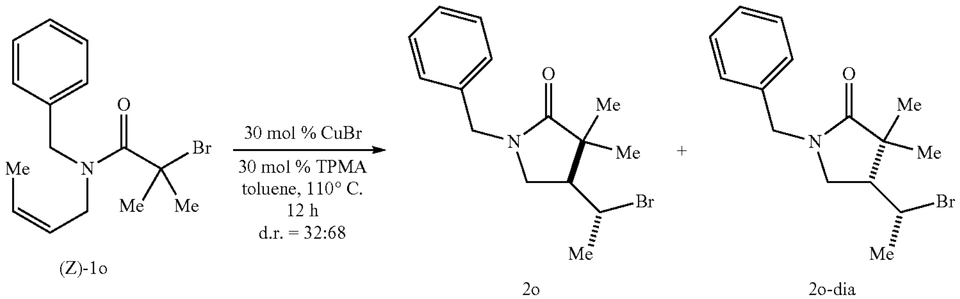 [SMILES: C/C=C\CN(Cc1ccccc1)C(=O)C(C)(C)Br ; C[C@@H](Br)[C@H]1CN(Cc2ccccc2)C(=O)C1(C)C ; C[C@@H](Br)[C@@H]1CN(Cc2ccccc2)C(=O)C1(C)C]

(Z)-1o 2o 2o-dia

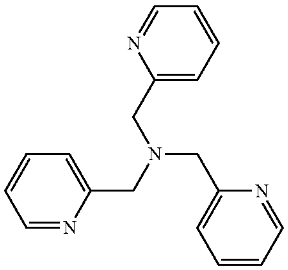

TPMA

| Substrate | d.r. (2o:2o-dia ratio) |
|---|---|
| (E)-1o | 39:61 [a] (38:62) [b] |
| (Z)-1o | 32:68 [a] (34:66) [b] |

[a] $^{1}H$ NMR analysis of the crude reaction mixture.

[b] HPLC analysis of the crude reaction mixture. As can be seen from these data, d.r. measured by HPLC is consistent with that by $^{1}H$ NMR analysis.

Mechanistic Studies

Synthetic route to radical clock substrate 1p is given below.

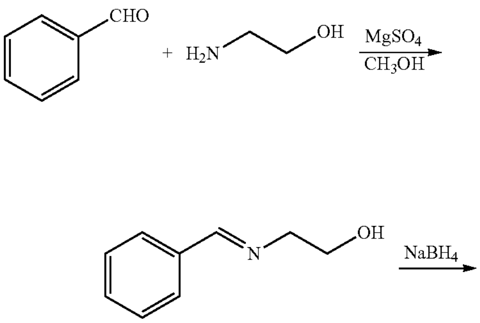

-continued

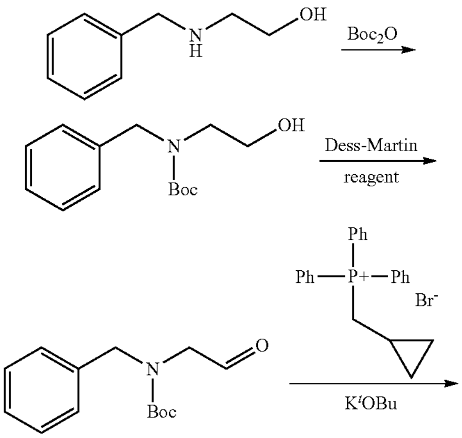

-continued

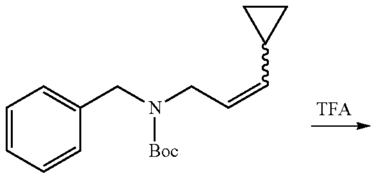

Z/E = 2.6:1

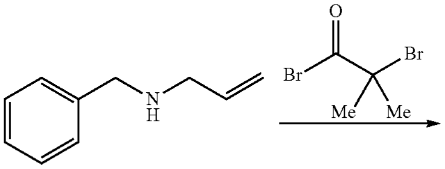

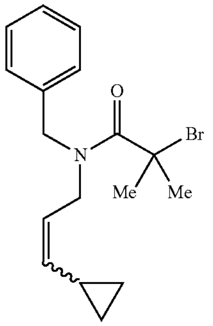

1p
Z/E = 2.6:1
78% yield

Result on hemin-catalyzed ring opening of radical clock substrate 1p is given

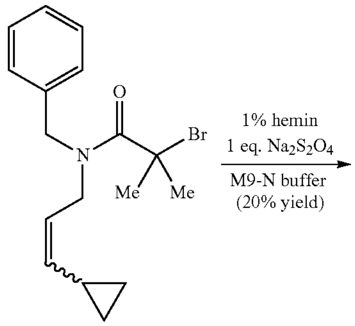

1p
Z/E = 2.6:1

-continued

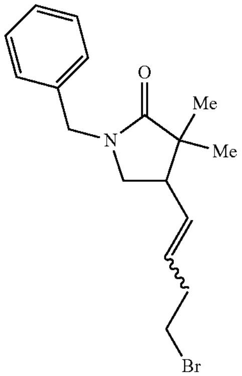

2p
mixture of E/Z isomers
(ratio = 5.7:1)

The conversion of radical clock substrate 1p to the ring opening product 2p using hemin as the catalyst indicated that the reaction proceeds through a radical-medicated mechanism. Use of protein catalysts provided ca. 2-4% yield of this product.

Mechanism of Dehydrohalogenation

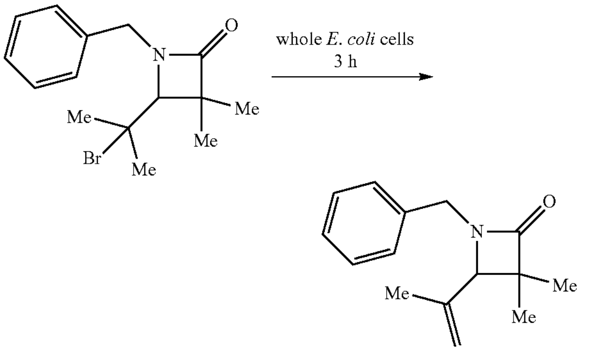

43% yield

Subjecting the ATRC bromide product to whole *E. coli* cells for 3 h resulted in the formation of 43% dehydrohalogenation product, suggesting that such elimination reactions occurs in the presence of *E. coli* cells in water. For comparison, subjecting this ATRC product to M9-N buffer (pH=7.4) for 3 h led to 33% elimination product, indicating that the presence of *E. coli* cells may accelerate this elimination reaction. In addition, a direct radical-polar crossover mechanism followed by deprotonation cannot be ruled out to account for the formation of this alkene product.

Amino acid sequences
Amino acid sequence of $P450_{ATRAsel}$ (SEQ ID NO. 1):
TIKEMPQPKTFGELKNLPLLNTDKPVQALMKIADELGEIFKFEAPGRVTRYLSSQRLIKE

ACDESRFDKNLSQALKFARDFTGDGLVTSWTHEKNWKKAHNILLPSFSQQAMKGYHAMMV

DIAVQLVQKWERLNADEHIEVSEDMTRLTLDTIGLCGFNYRFNSFYRDQPHPFIISMVRA

FDEVMNKLQRANPDDPAYDENKRQFQEDIKVMNDLVDKIIADRKARGEQSDDLLTQMLNG

KDPETGEPLDDGNIRYQIITFLQAGHEATSGLLSFALYFLVKNPHVLQKVAEEAARVLVD

PVPSYKQVKQLKYVGMVLNEALRLWPIAPAFSLYAKEDTVLGGEYPLEKGDEVMVLIPQL

-continued

HRDKTVWGDDVEEFRPERFENPSAIPQHAFKPFGNGQRASIGQQFALHEATLVLGMMLKH

FDFEDHTNYELDIKETLSLKPKGFVVKAKSKKIPLGGIPSPSTEQSAKKVRKKAENAHNT

PLLVLYGSNMGTAEGTARDLADIAMSKGFAPQVATLDSHAGNLPREGAVLIVTASYNGHP

PDNAKQFVDWLDQASADEVKGVRYSVFGCGDKNWATTYQKVPAFIDETLAAKGAENIADR

GEADASDDFEGTYEEWREHMWSDVAAYFNLDIENSEDNKSTLSLQFVDSAADMPLAKMHG

AFSTNVVASKELQQPGSARSTRHLEIELPKEASYQEGDHLGVIPRNYEGIVNRVTARFGL

DASQQIRLEAEEEKLAHLPLAKTVSVEELLQYVELQDPVTRTQLRAMAAKTVCPPHKVEL

EALLEKQAYKEQVLAKRLTMLELLEKYPACEMKFSEFIALLPSIRPRYYSISSSPRVDEK

QASITVSVVSGEAWSGYGEYKGIASNYLAELQEGDTITCFISTPQSEFTLPKDPETPLIM

VGPGTGVAPFRGFVQARKQLKEQGQSLGEAHLYFGCRSPHEDYLYQEELENAQSEGIITL

HTAFSRMPNQPKTYVQHVMEQDGKKLIELLDQGAHFYICGDGSQMAPAVEATLMKSYADV

HQVSEADARLWLQQLEEKGRYAKDVWAGLE
Note: His-tag or other tag can be added to sequence Amino acid sequence of $P450_{ATRAse2}$ (SEQ ID NO. 2):
TIKEMPQPKTFGELKNLPLLNTDKPVQALMKIADELGEIFKFEAPGRVTRYLSSQRLIK

EACDESRFDKNLSQGLKFLRDFLGDGLATSWTHEKNWKKAHNILLPSFSQQAMKGYHAMM

VDIAVQLVQKWERLNADEHIEVSEDMTRLTLDTIGLCGFNYRFNSFYRDQPHPFIISLVR

AVDEVMNKLQRANPDDPAYDENKRQFQEDIKVMNDLVDKIIADRKARGEQSDDLLTQMLN

GKDPETGEPLDDGNIRYQIITFLWAGHEGTSGLLSFALYFLVKNPHVLQKVAEEAARVLV

DPVPSYKQVKQLKYVGMVLNEALRLWPCVPAFSLYAKEDTVLGGEYPLEKGDEVMVLIPQ

LHRDKTVWGDDVEEFRPERFENPSAIPQHAFKPFGNGQRAAIGQQFALHEATLVLGMMLK

HFDFEDHTNYELDIKETFQLKPKGFVVKAKSKKIPLGGIPSPSTEQSAKKVRKKAENAHN

TPLLVLYGSNMGTAEGTARDLADIAMSKGFAPQVATLDSHAGNLPREGAVLIVTASYNGH

PPDNAKQFVDWLDQASADEVKGVRYSVFGCGDKNWATTYQKVPAFIDETLAAKGAENIAD

RGEADASDDFEGTYEEWREHMWSDVAAYFNLDIENSEDNKSTLSLQFVDSAADMPLAKMH

GAFSTLE
Note: His-tag or other tag can be added to sequence

Amino acid sequence of $P450_{ATRAse3}$ (SEQ ID NO. 3):
TIKEMPQPKTFGELKNLPLLNTDKPVQALMKIADELGEIFKFEAPGRVTRYLSSQRLIKE

ACDESRFDKNLSQALKFARDFTGDGLVTSWTHEKNWKKAHNILLPSFSQQAMKGYHAMMV

DIAVQLVQKWERLNADEHIEVSEDMTRLTLDTIGLCGFNYRFNSFYRDQPHPFIISMVRA

FDEVMNKLQRANPDDPAYDENKRQFQEDIKVMNDLVDKIIADRKARGEQSDDLLTQMLNG

KDPETGEPLDDGNIRYQIITFLQAGHAATSGLLSFALYFLVKNPHVLQKVAEEAARVLVD

PVPSYKQVKQLKYVGMVLNEALRLWPIAPAFSLYAKEDTVLGGEYPLEKGDEVMVLIPQL

HRDKTVWGDDVEEFRPERFENPSAIPQHAFKPFGNGQRASIGQQFALHEATLVLGMMLKH

FDFEDHTNYELDIKETIYLKPKGFVVKAKSKKIPLGGIPSPSTEQSAKKVRKKAENAHNT

PLLVLYGSNMGTAEGTARDLADIAMSKGFAPQVATLDSHAGNLPREGAVLIVTASYNGHP

PDNAKQFVDWLDQASADEVKGVRYSVFGCGDKNWATTYQKVPAFIDETLAAKGAENIADR

GEADASDDFEGTYEEWREHMWSDVAAYFNLDIENSEDNKSTLSLQFVDSAADMPLAKMHG

AFSTNVVASKELQQPGSARSTRHLEIELPKEASYQEGDHLGVIPRNYEGIVNRVTARFGL

DASQQIRLEAEEEKLAHLPLAKTVSVEELLQYVELQDPVTRTQLRAMAAKTVCPPHKVEL

EALLEKQAYKEQVLAKRLTMLELLEKYPACEMKFSEFIALLPSIRPRYYSISSSPRVDEK

QASITVSVVSGEAWSGYGEYKGIASNYLAELQEGDTITCFISTPQSEFTLPKDPETPLIM

-continued

```
VGPGTGVAPFRGFVQARKQLKEQGQSLGEAHLYFGCRSPHEDYLYQEELENAQSEGIITL

HTAFSRMPNQPKTYVQHVMEQDGKKLIELLDQGAHFYICGDGSQMAPAVEATLMKSYADV

HQVSEADARLWLQQLEEKGRYAKDVWAGLE
```

Note: His-tag or other tag can be added to sequence

Amino acid sequence of $P450_{ATRAse4}$ (SEQ ID NO. 4):

```
TIKEMPQPKTFGELKNLPLLNTDKPVQALMKIADELGEIFKFEAPGRVTRYLSSQRLIKE

ACDESRFDKNLSQALKFARDFAGDGLVTSWTHEKNWKKAHNILLPSFSQQAMKGYHAMMV

DIAVQLVQKWERLNADEHIEVSEDMTRLTLDTIGLCGFNYRFNSFYRDQPHPFIISMVRA

VDEVMNKLQRANPDDPAYDENKRQFQEDIKVMNDLVDKIIADRKARGEQSDDLLTQMLNG

KDPETGEPLDDGNIRYQIITFLLAGHEGTSGLLSFALYFLVKNPHVLQKVAEEAARVLVD

PVPSYKQVKQLKYVGMVLNEALRLWPVAPTFSLYAKEDTVLGGEYPLEKGDEVMVLIPQL

HRDKTVWGDDVEEFRPERFENPSAIPQHAFKPFGNGQRASIGQQFALHEATLVLGMMLKH

FDFEDHTNYELDIKETFQLKPKGFVVKAKSKKIPLGGIPSPSTEQSAKKVRKKAENAHNT

PLLVLYGSNMGTAEGTARDLADIAMSKGFAPQVATLDSHAGNLPREGAVLIVTASYNGHP

PDNAKQFVDWLDQASADEVKGVRYSVFGCGDKNWATTYQKVPAFIDETLAAKGAENIADR

GEADASDDFEGTYEEWREHMWSDVAAYFNLDIENSEDNKSTLSLQFVDSAADMPLAKMHG

AFSTNVVASKELQQPGSARSTRHLEIELPKEASYQEGDHLGVIPRNYEGIVNRVTARFGL

DASQQIRLEAEEEKLAHLPLAKTVSVEELLQYVELQDPVTRTQLRAMAAKTVCPPHKVEL

EALLEKQAYKEQVLAKRLTMLELLEKYPACEMKFSEFIALLPSIRPRYYSISSSPRVDEK

QASITVSVVSGEAWSGYGEYKGIASNYLAELQEGDTITCFISTPQSEFTLPKDPETPLIM

VGPGTGVAPFRGFVQARKQLKEQGQSLGEAHLYFGCRSPHEDYLYQEELENAQSEGIITL

HTAFSRMPNQPKTYVQHVMEQDGKKLIELLDQGAHFYICGDGSQMAPAVEATLMKSYADV

HQVSEADARLWLQQLEEKGRYAKDVWAGLE
```

Note: His-tag or other tag can be added to sequence

Cell Viability Assay

Figure 13:
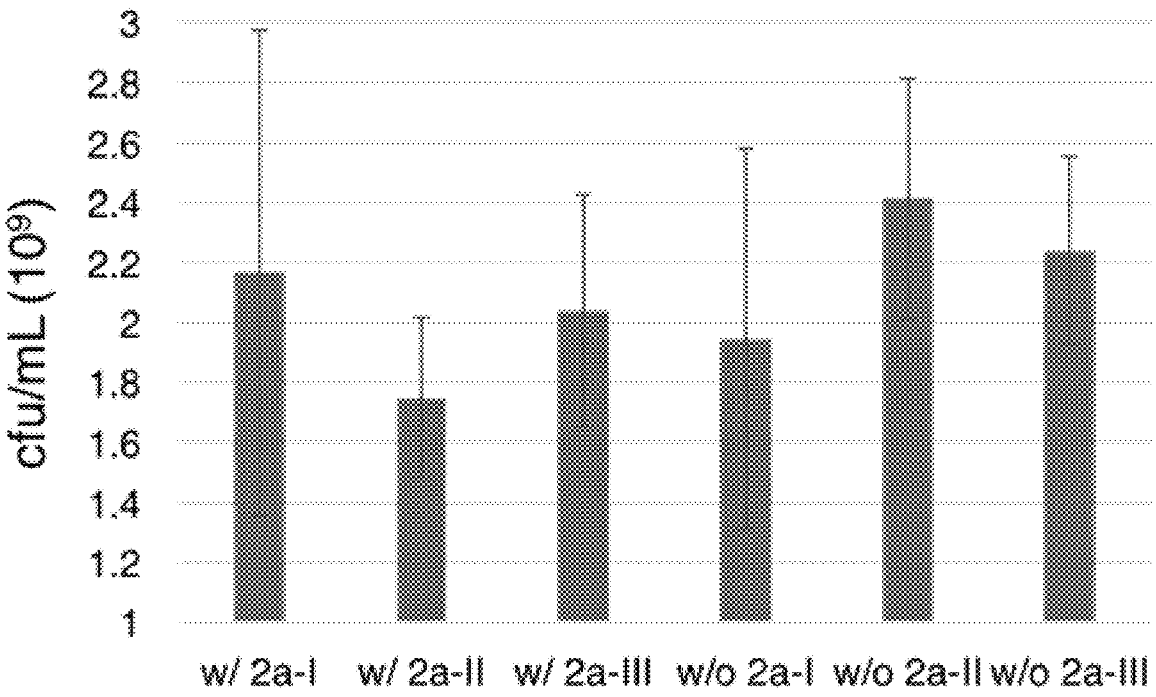
FIG. 13 provides a data graph depicting the effect of biocatalytic ATRA on *E. coli* cell viability, generated in accordance with various embodiments.

The colony forming units (cfu) of whole-cell reactions (+ substrate 1a) and controls without the substrate (– substrate 1a) were determined with biological replicates of triplicates using the procedure described below. Six 2 ml screw cap vials containing 380 μl suspension of *E. coli* cells harboring $P450_{ATRAse1}$ ($OD_{600}$=30) were transferred to an anaerobic chamber. To three of these vials were added substrate 1a (10 μL, 400 mM in EtOH). These vials were capped and shaken at 500 rpm in the anaerobic chamber (+ substrate 1a). The remaining three vials were capped and shaken in the absence of substrate (– substrate 1a). After 2.5 h, all six vials were removed from the anaerobic chamber. Aliquots of cell suspension were removed from the vials and subjected to serial dilution to obtain stock solutions of $10^6$-fold dilution. 50 μL of each stock solution was plated on LB (amp) agar plates and incubated at 37°° C. overnight. The cfu of the cell suspensions were calculated based on the colony counts of the $10^6$dilution plate (FIG. 13). No significant difference in cfu was observed in the presence and absence of substrate 1a. These results showed that biocatalytic ATRC does not markedly reduced the viability of *E. coli* cells.

Synthesis and Characterizations of Substrates

General procedure for the synthesis of substrates:

Route A

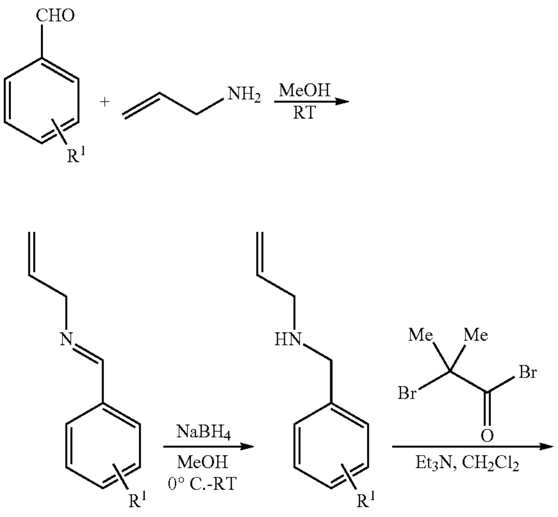

-continued

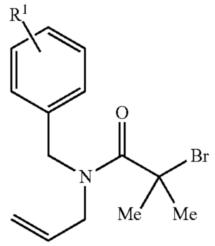

Route B

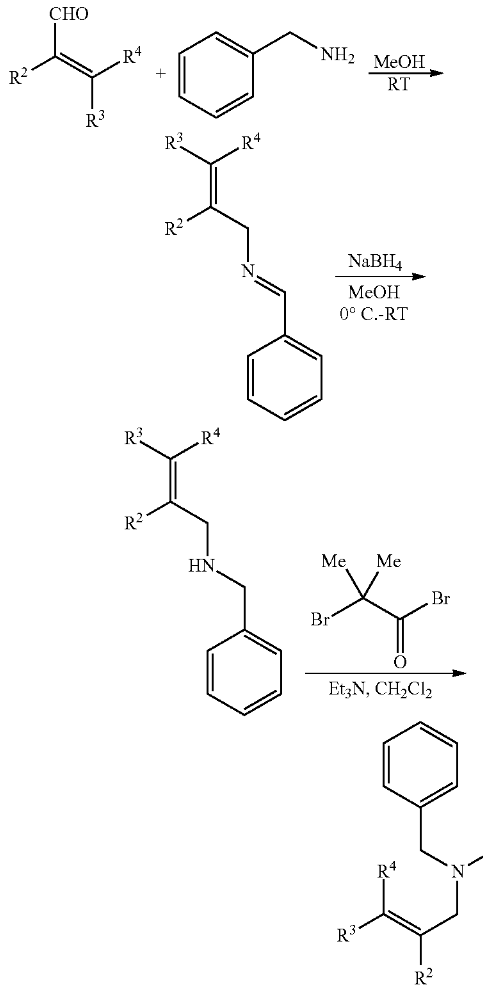

General Procedure A

At room temperature, the aldehyde (10 mmol, 1 equiv) and the amine (11 mmol, 1.1 equiv) were added to 40 mL MeOH (0.25 M). This mixture was stirred at room temperature for 3-12 h until GC analysis indicated full conversion of the aldehyde substrate. $NaBH_4$ (16 mmol, 1.6 equiv) was slowly added, and the reaction mixture was allowed to stir at room temperature for 10 min. MeOH was removed in vacuo with the aid of a rotary evaporator. The solid residue was diluted with EtOAc and quenched with 1 M NaOH (aq.). The organic and aqueous layers were separated, and the aqueous layer was extracted with EtOAc for three times. Combined organic layers were washed with brine and dried over $MgSO_4$. Solvent was removed in vacuo with the aid of a rotary evaporator. The crude amine product was directly used for the next step without further purification.

A round bottom flask containing the crude amine was evacuated and backfilled with $N_2$ and this process is repeated for three times. The amine was then dissolved in $CH_2Cl_2$ (0.50 M). $Et_3N$ (2.0 equiv) was added. At 0° C., α-bromoisobutyryl bromide was slowly added. The reaction mixture was allowed to warm to room temperature, stirred for an additional 1 h, and then quenched by the addition of water. $CH_2Cl_2$ was added to dilute the reaction mixture. The organic layer was separated, washed with water and 1 M HCl (aq.), and dried over $MgSO_4$. Solvent was removed in vacuo with the aid of a rotary evaporator. The crude amide product was purified by flash column chromatography with the aid of a Biotage Isolera.

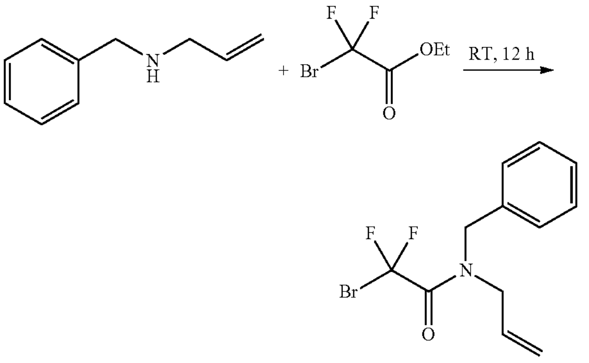

General Procedure B

At room temperature, Ethyl bromodifluoroacetate (6 mmol, 1.2 equiv) was added to the amine (5 mmol, 1 equiv) at 0° C. The mixture was allowed to warm to room temperature and stirred for 12 h. The reaction mixture was diluted with 1 M HCl and extracted with EtOAc (3×). The organic layer was separated, combined, and dried over $MgSO_4$. Solvent was removed in vacuo with the aid of a rotary evaporator. The crude amide product was purified by flash column chromatography with the aid of a Biotage Isolera.

Synthesis of Geometrically Well-Defined (E)- and (Z)-lo:

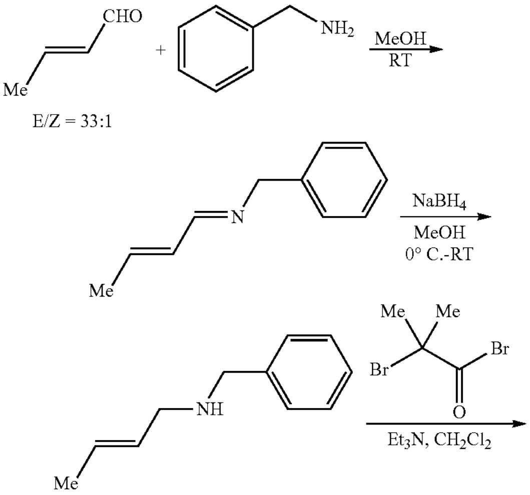

-continued

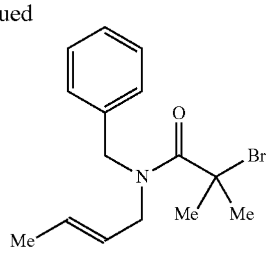

(E)-1o was synthesized from commercial crotonaldehyde (predominantly trans-, $^1H$ NMR analysis indicated E/Z=33:1) using General Procedure A described above. The E/Z ratio of the reductive amination product was determined to be 12:1 by $^1H$ NMR analysis.

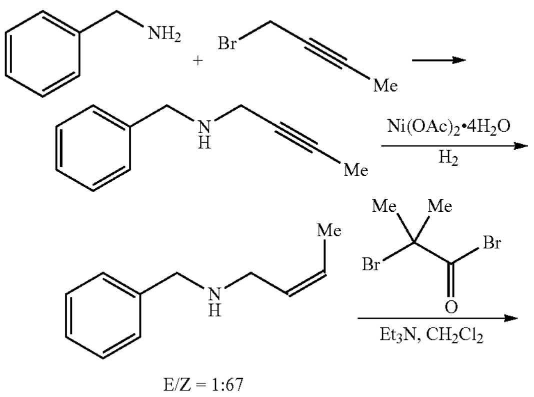

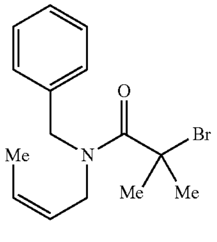

(Z)-1o is synthesized as follows. At room temperature, propargyl bromide (1.0 equiv.) was added slowly to benzylamine, and the reaction mixture was allowed to stir at room temperature for 20 h. The crude reaction mixture was then purified by flash column chromatography with the aid of a Biotage Isolera (1:1 EtOAc/hexanes, with 1% $Et_3N$) to afford N-benzylbut-2-yn-1-amine as a colorless oil.

To a round bottom flask were added nickel (II) acetate tetrahydrate (2.9 mmol, 0.25 equiv) and MeOH (4 mL). The round bottom was evacuated and backfilled with $H_2$ and this sequence was repeated for a total of three times. At 0° C., a MeOH solution of sodium borohydride (2.9 mmol, 0.25 equiv, 4 mL) was slowly added, and the suspension was stirred at room temperature for 15 min. N-Benzylbut-2-yn-1-amine (11.6 mmol, 1 equiv) and ethylene diamine (5.8 mmol, 0.5 equiv) in MeOH (12 mL) were added and the mixture was stirred under $H_2$ at room temperature. The reaction was allowed to proceed at room temperature for ca. 1 h and monitored by TLC analysis every 10 min after the first hour. (Note: Overreduction of the product will result in the formation of N-butylbenzylamine. Thus, carefully monitoring the progress of the semihydrogenation reaction by TLC analysis is the key to avoid overreduction.) Once the starting material is fully consumed, $H_2$ balloon was immediately removed. Solvent was removed in vacuo with the aid of a rotary evaporator and the solid residue was taken up with EtOAc and washed with water. The aqueous layer was separated and extracted with EtOAc for an additional three times. The organic layers were combined, dried over $MgSO_4$ and concentrated in vacuo with the aid of a rotary evaporator. The crude product was used directly in the next step without purification. The E/Z ratio of the crude amine product was determined to be 1:67. The final acylation step is performed by following General Procedure A.

Characterization Data for Atom Transfer Radical Cyclization Products

General Procedure for the Synthesis of Racemic Products

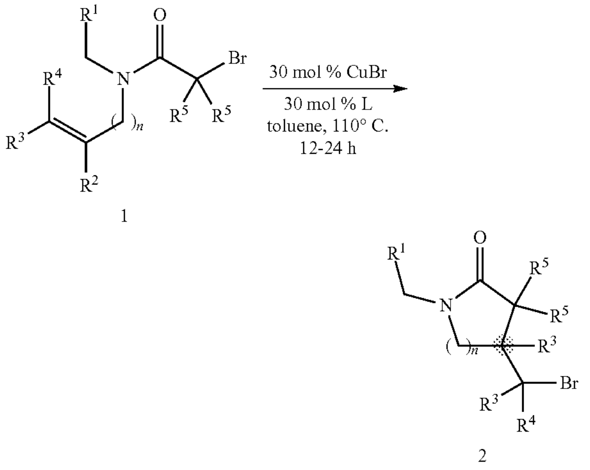

(L1)

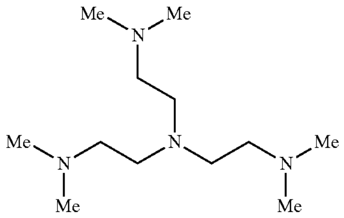

Me6TREN (L2)

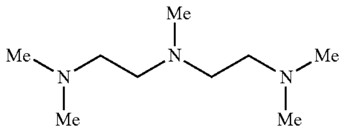

PMEDTA (L3)

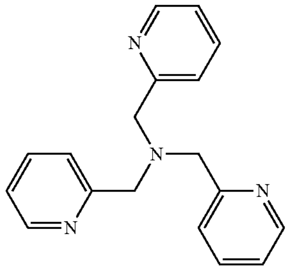

TPMA

Racemic products were synthesized on a 0.2-5.0 mmol scale using 30 mol % CuBr and 30 mol % L in 70-80% yield.

Cu catalysts composed of L1-L3 provided the desired racemic compound with varying yields.

General Procedure: CuBr (30 mol %), L (30 mol %), and the substrate were charged to a reaction tube. Toluene (0.1 M) was added, and the resulting mixture was subjected to three freeze-pump-thaw cycles. The reaction tube was then placed in an oil bath at 110° C. for 12-24 h. After the reaction went to completion, the crude reaction mixture was directly subjected to column chromatography by elution with hexane to hexane/ethyl acetate (2:1) to give the corresponding product.

Enantioenriched enzymatic products were synthesized by preparative scale enzymatic reaction using the general procedure described above.

Procedure for Derivatization Reactions and Characterization Data

Azidation

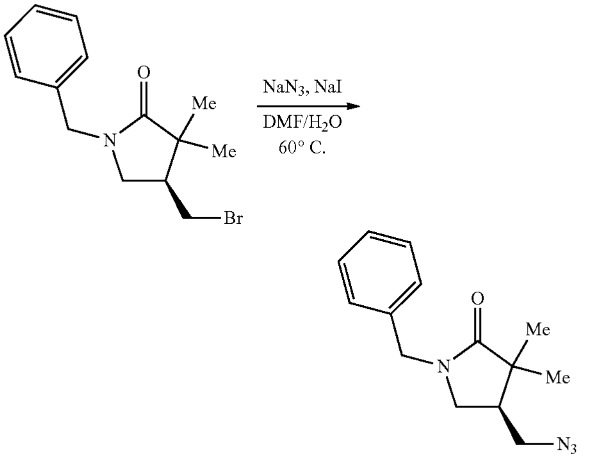

A screw-cap vial was charged with (R)-1-benzyl-4-(bromomethyl)-3,3-dimethylpyrrolidin-2-one (59 mg, 1.0 equiv, 0.2 mmol), $NaN_3$ (65 mg, 5.0 equiv. 1.0 mmol), and NaI (150 mg, 5.0 equiv, 1.0 mmol). DMF (1 mL) and $H_2O$ (200 μL) were then added to the vial. The reaction mixture was stirred for 16 h at 60° C. The reaction mixture was diluted with 2.5 mL of 1.0 M NaOH (aq.), extracted with EtOAc and dried over $MgSO_4$. Solvent was removed in vacuo and the crude product was purified by Biotage (10 g SNAP cartridge, 0-33% EtOAc/hexanes for 8 CV, then 33% EtOAc/hexanes for 5 CV) to afford the product as a colorless oil (0.2 mmol scale, 42 mg, 71% yield).

Cyanation

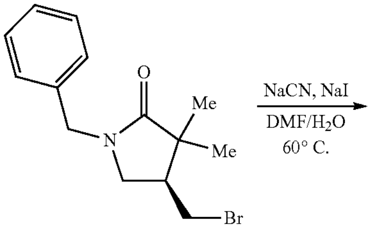

-continued

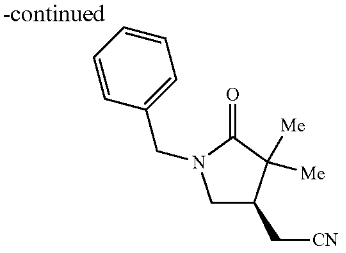

A screw-cap vial was charged with (R)-1-benzyl-4-(bromomethyl)-3,3-dimethylpyrrolidin-2-one (59 mg, 1.0 equiv, 0.2 mmol), NaCN (49 mg, 5.0 equiv, 1.0 mmol), and NaI (150 mg, 5.0 equiv, 1.0 mmol). DMF (1 mL) and $H_2O$ (200 μL) were then added to the vial. The reaction mixture was stirred for 16 h at 60° C. The reaction mixture was diluted with 2.5 mL of 1.0 M NaOH (aq.), extracted with EtOAc and dried over $MgSO_4$. Solvent was removed in vacuo and the crude product was purified by Biotage (10 g SNAP cartridge, 0-50% EtOAc/hexanes for 8 CV, then 50% EtOAc/hexanes for 5 CV) to afford the product as a white solid (0.2 mmol scale, 47 mg, 79% yield).

Xanthation

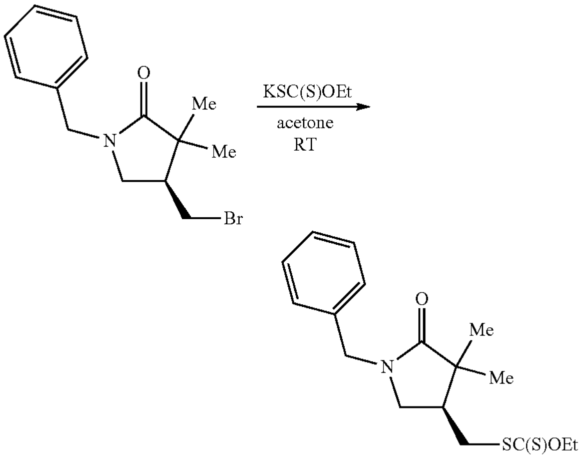

A screw-cap vial was charged with (R)-1-benzyl-4-(bromomethyl)-3,3-dimethylpyrrolidin-2-one (30 mg, 1.0 equiv, 0.1 mmol) and potassium ethyl xanthate (1.5 equiv). Acetone (0.5 mL) was then added. The mixture was at room temperature stirred overnight and then concentrated in vacuo. EtOAc was added, and the organic layer was washed with water. The aqueous layer was then extracted with ethyl acetate (3×) and dried with $MgSO_4$. Solvent was removed in vacuo and the crude product was purified by Biotage (10 g SNAP cartridge, 0-50% EtOAc/hexanes for 8 CV, then 50% EtOAc/hexanes for 5 CV) to afford the product as a colorless oil (0.1 mmol scale, 21 mg, 63% yield).

Computational Studies

Computational Details

All density functional theory (DFT) calculations were carried out using the Gaussian 16 program (59). Geometries of intermediates and transition states were optimized using the dispersion-corrected (U)B3LYP-D3 functional (60-62) with a mixed basis set of LANL2DZ for Fe and 6-31G(d) for other atoms in the gas phase. Vibrational frequency calculations were performed for all stationary points to confirm if each optimized structure is a local minimum or a transition state structure. All optimized transition state structures have only one imaginary (negative) frequency, and all minima (reactants, products, and intermediates) have no imaginary frequencies. The (U)B3LYP-D3 functional with a mixed basis set of LANL2TZ(f) (63) for Fe and 6-311+G(d,p) for other atoms was used for single-point energy calculations in solution. Solvation energy corrections were calculated in chlorobenzene ($\varepsilon$=5.6968) solvent with the SMD continuum solvation model (64) based on the gas-phase optimized geometries. The solvent environment was chosen based on recommendations from previous computational studies of enzymatic reactions to mimic the relative permittivity in enzyme active sites (65, 66). The C—Br and Fe—Br bond dissociation enthalpies (BDEs) at 298 K were calculated at the same level of theory [(U)B3LYP-D3/LANL2TZ(f)-6-311+G(d,p)/SMD//(U)B3LYP-D3/LANL2DZ/6-31G(d)]. Gibbs free energies were calculated at the standard conditions (298 K, 1 M solution). Truhlar's quasi-harmonic corrections (67) were applied for vibrational entropy calculations using 100 $cm^{-1}$ as the frequency cutoff using GoodVibes (68). It should be noted that entropic corrections were calculated using gas-phase formulas. Although this is a standard practice in computing organic reaction energy profiles, the entropic components in the bimolecular reactions are expected to be overestimated, because the translational and rotational entropies of substrates in the enzyme active site are much less than those in the gas phase. Accurate calculations of entropies in enzyme catalysis require extensive molecular dynamics simulations at different temperatures (69), which is beyond the scope of the present study. It should be noted that the key objectives of the present computational study, including the spin states of the Fe catalyst and intermediates, geometries of the halogen atom abstraction transition states, thermodynamics of the halogen atom abstraction, and the endo/exo selectivity, are not expected to be affected by entropic effects. 3D images of optimized structures were prepared using CYLView and POV-Ray.

The explicitly correlated local coupled cluster method, PNO-LCCSD(T)-F12, was used as references to benchmark DFT methods. The PNO-LCCSD(T)-F12 calculations were performed using Molpro 2020.2 (70, 71). In the PNO-LCCSD(T)-F12 calculations, a mixed basis set of aug-cc-pwCVTZ for Fe, ECP10MDF effective core potential along with aug-cc-pwCVTZ-PP for Br, and VDZ-F12 for other atoms. Def2-TZVPP/JKFIT (Fe), aug-cc-pVTZ/JKFIT (Br), and AVTZ/JKFIT (other atoms) were used as the fitting auxiliary basis to compute the Fock matrix and as the RI basis set. For the density fitting for other calculations of all other 2-electron integrals, the aug-cc-pwCVTZ/MP2FIT (Fe), aug-cc-pVTZ/MP2FIT (Br), and AVDZ/MP2FIT (other atoms) basis sets were used. These basis sets are similar to those used by Werner et al. in recent computational studies (72, 73). In the PNO-LCCSD(T)-F12 calculations of the Fe complex, four outer core orbitals (Fe, 3s3p) were correlated (73). T1/D1 diagnostic values were calculated in all PNO-LCCSD(T)-F12 calculations in the benchmark study to evaluate the multireference character of these complexes. According to the criteria recommended by Wilson et al. for 3d transition metals, T1 values smaller than 0.05 and D1 values smaller than 0.15 would suggest that the single reference PNO-LCCSD(T)-F12 method is adequate to describe the molecular ground state (74). The computed T1/D1 diagnostic values of most complexes in the present study are smaller than the recommended thresholds (see later for details), indicating that the multireference character of these complexes is not important, and thus the coupled cluster method should predict reliable energetics.

In the DFT and PNO-LCCSD(T)-F12 calculations, porphine was used as a model for the porphyrin ligand and methoxy (OMe) was used as the model for the axial serine ligand. Similar model systems have been used in previous computational studies of heme-containing enzymes (75-77). For each Fe complex and transition state, three different spin states were calculated (high-spin, quintet or sextet; intermediate-spin, triplet or quartet; and low-spin, doublet or singlet). Wavefunction stability tests were carried out with the "stable=opt" keyword to ensure all the open-shell calculations adopted stable wavefunctions. The stability test suggested that the closed-shell singlet wavefunctions of Fe complexes are unstable. All singlet Fe complexes in this study are open-shell singlet without $\alpha/\beta$ symmetries.

Benchmark of DFT Methods for Spin-State Energies of Iron-Porphyrin Complexes

The performance of DFT methods for spin-state energies of iron complexes, including model iron-heme complexes, has been extensively studied (78, 79). Here, we performed benchmark calculations of the Fe(II) complex 4 in singlet ($^{1}_{4}$), triplet ($^{3}_{4}$), and quintet ($^{5}4$) spin states and the Fe(III) □Br complex 6 in doublet ($^{2}_{6}$), quartet ($^{4}_{6}$), and sextet ($^{6}_{6}$) spin states to identify suitable DFT methods for energetics of the iron-porphyrin complexes in the present system (Table S12). To obtain accurate single-point energies as references, we performed the explicitly correlated local coupled-cluster calculations (PNO-LCCSD(T)-F12) using the B3LYP-D3-optimized geometries. All benchmark calculations were performed in the gas phase.

PNO-LCCSD(T)-F12 calculations predicted that the high-spin state (quintet) of 4 is highly favorable. The quintet Fe(II) catalyst $^{5}4$ is 22.1 kcal/mol more stable than the triplet $^{3}_{4}$ and 23.5 kcal/mol more stable than its singlet $^{1}_{4}$. The Fe(III)□Br complex prefers the low-spin doublet state in the gas phase, although the sextet ($^{6}_{6}$) is only 3.0 kcal/mol higher in energy than the doublet ($^{2}_{6}$). The quartet ($^{4}_{6}$) is 12.3 kcal/mol less stable than the sextet $^{6}_{6}$. All DFT methods tested correctly predicted the high-spin quintet state of 4 is the most stable. However, only (U)B3LYP-D3, (U)OLYP (80, 81), and (U)MN15 (82) correctly predicted the lowest-energy spin state for 6. (U)OPBE (83, 84) and (U)ωB97X-D (85) predicted the high-spin sextet state is slightly more stable than the doublet. (U)M06 (86) significantly overestimated the stability of the high-spin sextet state of 6. We chose (U)B3LYP-D3 in the following DFT calculations because it predicted the correct spin states for both 4 and 6 and provided the best agreement with the PNO-LCCSD(T)-F12 spin-state energies (i.e. with the smallest mean absolute error, MAE).

TABLE 13

| Benchmark of DFT methods. | | | | | | | |
|---|---|---|---|---|---|---|---|
| | PNO-CCSD(T)-F12 | B3LYP-D3 | OLYP | OPBE | ωB97X-D | M06 | MN15 |
| $\Delta E_{LH}(4)$ | −23.5 | −16.0 | −14.5 | −15.8 | −19.9 | −38.2 | −16.9 |
| $\Delta E_{IH}(4)$ | −22.1 | −10.7 | −7.9 | −7.9 | −16.6 | −16.3 | −4.2 |
| $\Delta E_{LH}(6)$ | 3.0 | 1.4 | 0.2 | −0.7 | −0.1 | −24.6 | 10.2 |
| $\Delta E_{IH}(6)$ | −12.3 | −6.2 | −5.9 | −7.3 | −7.5 | −16.6 | 2.8 |
| MAE(ΔΔE) | | 6.7 | 8.1 | 7.7 | 4.3 | 13.1 | 11.7 |

[a]All energies are in kcal/mol. For 4, $\Delta E_{LH} = E_{quintet} - E_{singlet}$, $\Delta E_{IH} = E_{quintet} - E_{triplet}$. For 6, $\Delta E_{LH} = E_{sextet} - E_{doublet}$, $\Delta E_{IH} = E_{sextet} - E_{quartet}$, $\Delta\Delta E = \Delta E_{DFT} - \Delta E_{PNO\text{-}CCSD(T)\text{-}F12}$. Geometries were optimized at the (U)B3LYP/6-31G(d)-LANL2DZ level of theory in gas phase at the corresponding spin state.

The T1/D1 diagnostic values of all Fe complexes are below the threshold values (T1<0.05, D1<0.15), except for $^{2}6$ where the D1 value (0.183) is slightly higher than the threshold (Table S2). The small T1/D1 diagnostic values of these iron complexes indicate their multireference character is not important, and thus the PNO-LCCSD(T)-F12 results are expected to be reliable as the energy references to benchmark DFT methods.

TABLE 14

| Diagnostics of multireference character. | | | | | | |
|---|---|---|---|---|---|---|
| Diagnostics | $^{1}4$ | $^{3}4$ | $^{5}4$ | $^{2}6$ | $^{4}6$ | $^{6}6$ |
| T1 | 0.022 | 0.019 | 0.015 | 0.025 | 0.023 | 0.020 |
| D1 | 0.137 | 0.099 | 0.056 | 0.183 | 0.145 | 0.114 |

Alternative Substrate Activation Pathways

In addition to the inner-sphere electron transfer (i.e. bromine atom abstraction) pathway, transition metal-mediated carbon-halogen bond activation of alkyl halides may also occur via three-membered oxidative addition, $S_N2$-type of oxidative addition, or outer-sphere single electron transfer. Because the Fe(II)-porphine complex has only one available coordination site to interact with the sterically crowded tertiary alkyl bromide substrate, the concerted three-membered oxidative addition and the $S_N2$-type of oxidative addition are unlikely to take place. The modified Marcus theory was used to estimate the barriers for the outer-sphere single electron transfer pathway. Geometry optimization of the radical anion of the alkyl bromide substrate 1a leads to direct dissociation of the C—Br bond to form an alkyl radical and a bromide anion, indicating that the radical anion of 1a is unstable and the outer-sphere electron transfer would lead to separated alkyl radical and bromide anion in a concerted process, known as dissociative electron transfer (DET) or concerted outer-sphere electron transfer (OSET-C). Therefore, Saveant's modified Marcus theory was used to calculate the activation free energy of this dissociative electron transfer pathway.

Figure 14:
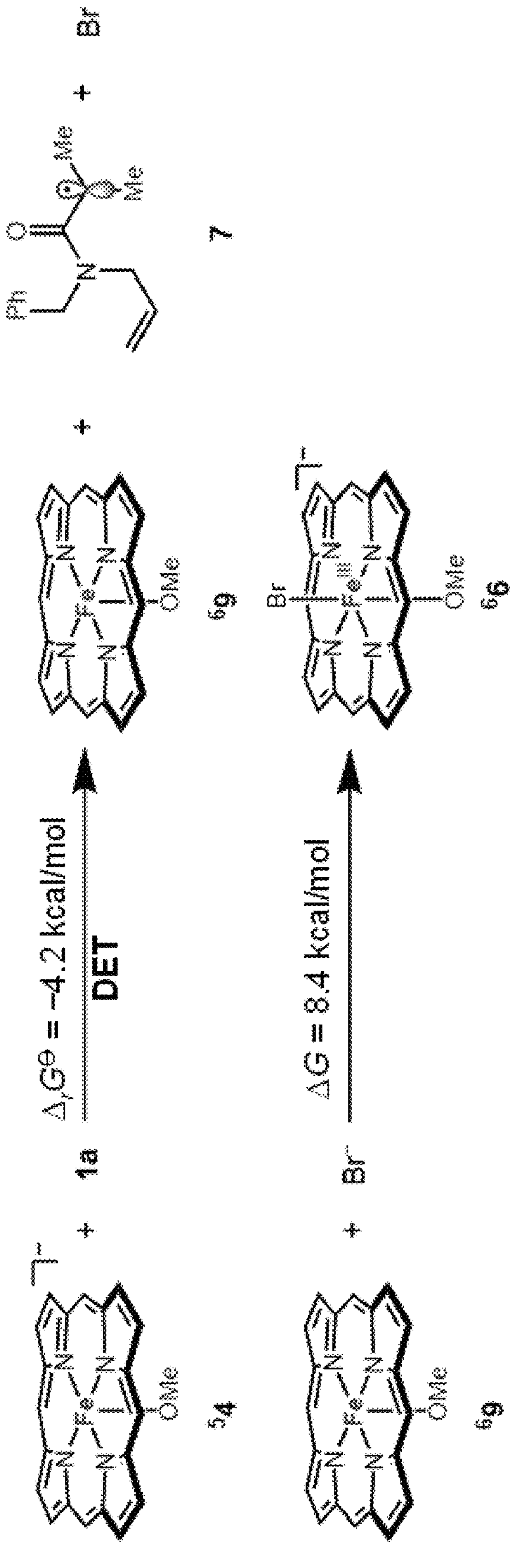
FIG. 14 provides a schematic of a dissociative electron transfer (DET) mechanism in accordance with various embodiments.

In the DET pathway (FIG. 14), the electron transfer occurs with simultaneous alkyl halide bond dissociation to form radical 7 and the Br— anion. The Br— anion subsequently coordinates to the Fe(III) center in 9 to form ferric bromide species 6. The activation Gibbs free energy of the DET step is given by $$G^{\ddagger}_{DET} = \Delta G^{\ddagger}_{0}\left(1 + \frac{\Delta_r G^{\ominus} - D_p}{4\Delta G^{\ddagger}_{0}}\right)^2$$

-continued $$\Delta G^{\ddagger}_{0} = \frac{\left(\sqrt{BDE_{1a}} - \sqrt{D_p}\right)^2 + l_0}{4}$$

where $$\Delta G^{\ddagger}_{0}$$

is the the intrinsic barrier; $\Delta G^{\ominus}$=−4.2 kcal/mol is the DFT-calculated reaction energy of the DET process; $D_p$ is the interaction energy between 7 and $Br^-$ in the solvent cage, because there is no available experimental data of $D_p$ (usually a small value close to 0), $D_p$=0 kcal/mol is used in our calculation (91); $BDE_{1a}$=56.4 kcal/mol is the bond dissociation enthalpy of the C(sp$^3$)-Br bond of 1a; $l_0$ is the solvent reorganization energy (92, 93) that can be calculated as follows:

$$\lambda_0 = \frac{N_A e^2}{4\pi\varepsilon_0}\left(\frac{1}{n_D^2} - \frac{1}{\varepsilon_S}\right)\left(\frac{1}{2r_D} + \frac{1}{2r_A} - \frac{1}{R}\right)$$

where $n_D$=1.52 and $\varepsilon_s$=5.6968 are refractive index and dielectric constants of chlorobenzene solvent, respectively. $\varepsilon_0$ is the vacuum permittivity. $r_D$ and $r_A$ are the hard-sphere radii of the electron donor ($^{5}4$, 5.7 Å) and acceptor (1a, 4.2 Å), respectively, calculated using the "volume" keyword in Gaussian 16.

Thus, $$\lambda_0 = \frac{6.02\times10^{23}\times\left(1.6\times10^{-19}\right)^2\times2.39\times10^{6}}{4\pi\times\left(8.85\times10^{-12}\right)}\left(\frac{1}{1.52^2} - \frac{1}{5.6968}\right)\left(\frac{1}{2\times5.7} + \frac{1}{2\times4.2} - \frac{1}{5.7+4.2}\right) = 9.0\ \text{kcal/mol}$$

It should be noted that because the "solvent reorganization energy" $\lambda_0$ was calculated using the model Fe-porphyrin catalyst in a non-polar solvent (εs=5.6968), this value may not represent the exact reorganization energy in an enzymatic environment. Calculating reorganization energies in enzymatic reactions requires the calculations of free energy curve on the diabatic product energy surface, which is often calculated using QM/MM. Although these calculations are beyond the scope of the present study, it should be noted that reorganization energies in engineered enzymes are often higher than those in wild-type enzymes and thus may lead to higher barriers to the electron transfer.

$$\Delta G_0^{\ddagger} = \frac{\left(\sqrt{BDE_{2a}} - \sqrt{D_p}\right)^2 + l_0}{4} = \frac{\left(\sqrt{56.4} - \sqrt{0}\right)^2 + 9.0}{4} = 16.4\ \text{kcal/mol}$$

$$\Delta G_{DET}^{\ddagger} = \Delta G_0^{\ddagger}\left(1 + \frac{\Delta_r G^{\ominus} - D_p}{4\Delta G_0^{\ddagger}}\right)^2 = 16.4 \times \left(1 + \frac{-4.2}{4 \times 16.4}\right)^2 = 14.4\ \text{kcal/mol}$$

These results suggest that the DET pathway requires 14.4 kcal/mol activation free energy with respect to $^5$4 and 1a. Previous computational studies indicated that the DET pathway in the reaction of $Cu^I$/TPMA catalyst and α-bromoisobutyrate requires a much higher barrier (>23 kcal/mol) and the ISET (inner-sphere single electron transfer, a.k.a. halogen atom abstraction) pathway with the Cu catalyst is comparable to the model Fe catalyst in the present study. Therefore, these results indicate that DET may be another viable pathway for the Fe catalyst, while with the $Cu^I$/TPMA catalyst, the reaction can only proceed via the ISET pathway due to the high DET barrier. Although it is challenging to directly compare the kinetics of the DET and ISET pathways in the present study because the barriers were calculated using different theories (Marcus theory vs transition state theory), the computational results so far suggest that the C—Br bond cleavage step is best described as an ISET process due to the following reasons. First, the computed barrier for ISET ($^5$TS1, $\Delta G^{\ddagger}$=17.7 kcal/mol) was based on a model Fe catalyst in the absence of the enzyme environment (75). This barrier includes the 4.1 kcal/mol free energy required to form the substrate complex (5). In the enzyme-catalyzed reactions, the substrate binding to form reactant complex is expected to be more favorable, despite the low concentration of the enzyme catalyst. The ISET TS ($^5$TS1) is only 13.6 kcal/mol higher than the substrate complex 5, indicating a faster reaction rate under saturation kinetics when 5 is the resting state prior to the C—Br bond cleavage. Second, the DET barrier calculated in a non-polar solvent environment may be lower than the barrier in an enzymatic environment because the reorganization energies are often relatively high in engineered enzymes (see above). Lastly, the ISET and DET pathways actually share many features—they both involve concerted electron-transfer and C—Br bond cleavage and they form the same products (6 and 7). The only difference is whether there is an inner-sphere interaction between the Br atom and the Fe center during the C—Br bond cleavage. Because the Fe catalyst is relatively rigid and has an empty coordination site, the Br—Fe interaction is expected to be thermodynamically favorable. The binding of the alkyl bromide substrate 1a to the Fe(II) catalyst (4) to form 5 is exothermic (ΔH=−7.3 kcal/mol). Distortion/interaction model analysis revealed that the interaction energies between 1a and 4 are −9.8 and −14.5 kcal/mol in the reactant complex 5 and the ISET transition state (TS1), respectively. On the other hand, the distortion energy of the Fe-porphine complex is small ($\Delta E_{dis}$=0.2 and 6.3 kcal/mol in 5 and TS1, respectively). These results suggest that the inner-sphere Br—Fe coordination is energetically favorable due to favorable interaction energies and relatively small distortion of the Fe-porphine complex. It should be noted that one scenario that could promote the DET pathway is the stabilization of the bromide anion via electrostatic or hydrogen bonding interactions with active site residues. This possibility is being investigated in our laboratories using molecular dynamics simulations. Taken together, the computational studies in the present study demonstrated that the Fe-porphine complex is a competent catalyst to promote C—Br bond cleavage to generate alkyl radical intermediate. This process may occur via either an inner-sphere single electron transfer (ISET) or an outer-sphere dissociative electron transfer (DET) mechanism, depending on whether the Fe center or the active site residues are more effective in stabilizing the bromide anion. The calculations indicate that the interaction between Br and the Fe center is energetically favorable and requires small distortion of the Fe catalyst, supporting an ISET mechanism. However, the DET pathway cannot be completely ruled out and warrants further studies using molecular dynamics simulations. Because the ISET and DET pathways share many mechanistic features and lead to the same products after the C—Br bond cleavage, the uncertainty of the C—Br bond cleavage mechanism will not affect the key conclusions discussed in the present study, including the spin-states of the Fe(II) catalyst and the Fe(III) intermediate, the thermodynamics of the C—Br bond cleavage/formation steps, factors promoting the radical initiation, and the exo-lendo selectivity in the cyclization step.

Figure 15:
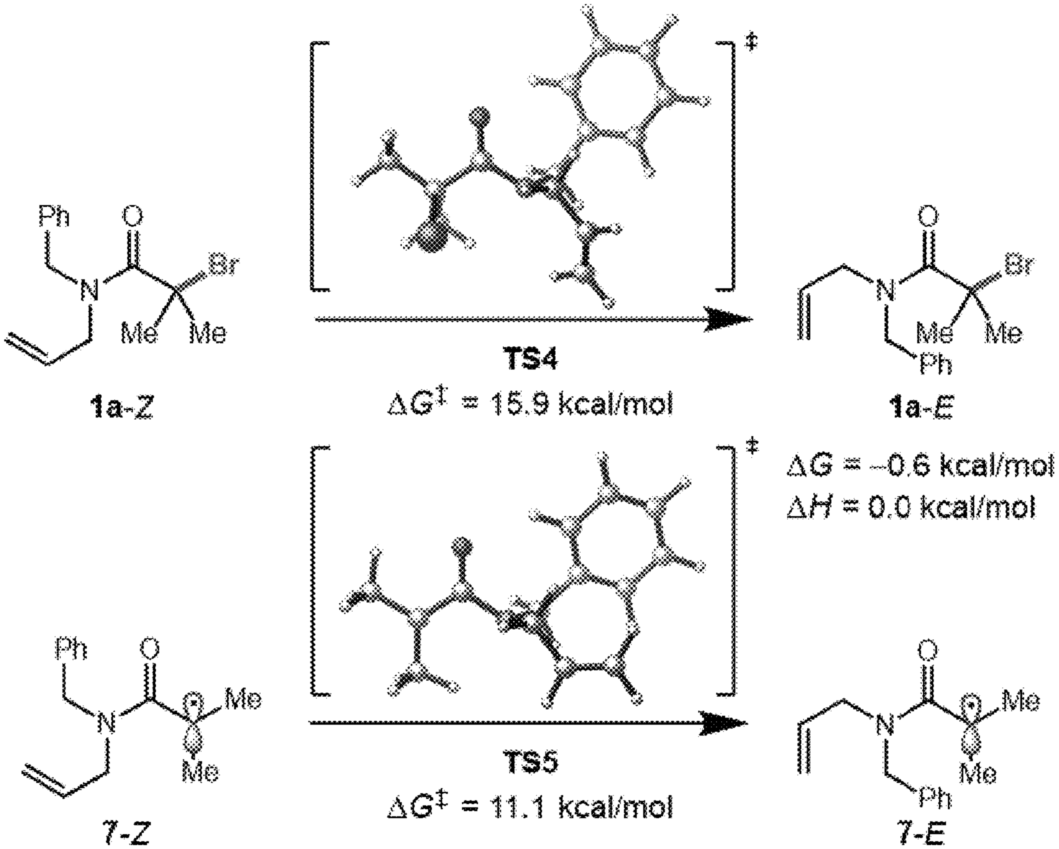
FIG. 15 provides a schematic of amide bond rotation barriers of chemical formula 1a and the radical intermediate 7 in accordance with various embodiments.
Figure 16:
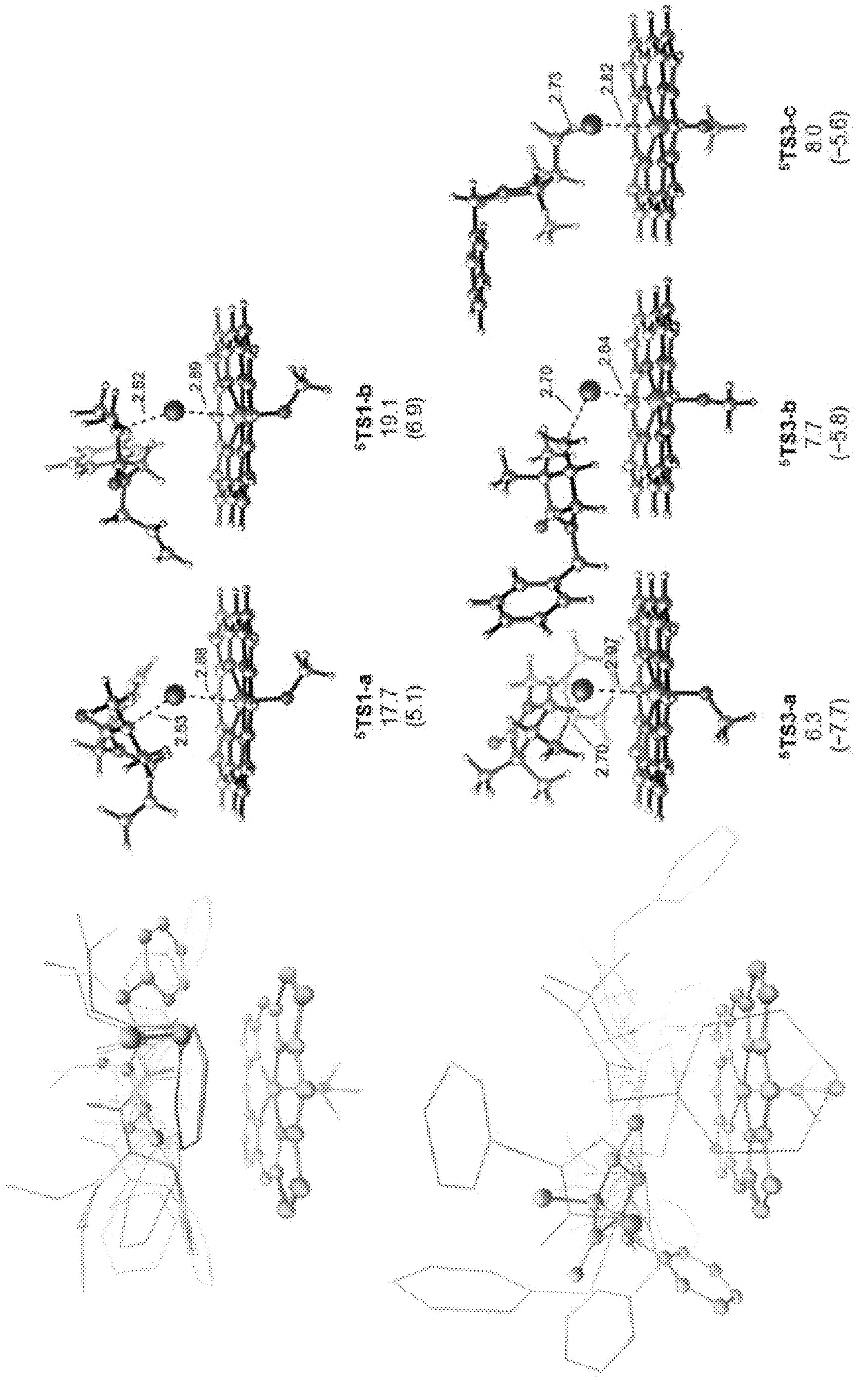
FIG. 16 provides a schematic depicting an overlay of the low-energy conformers within 3.5 kcal/mol with respect to the most stable conformers of $^5$TS1 and $^5$TS3 and the selected transition state conformers in accordance with various embodiments. The lowest energy conformers are shown in green ball and sticks. The higher energy conformers are shown in wireframe. All Gibbs free energies and enthalpies (in parentheses) are with respect to $^{5}4$ and 1a, in kcal/mol.

Both the Z and E rotamers of the amide substrate 1a and the alkyl radical intermediate 7 were calculated (FIG. 15). The activation free energy of the amide bond rotation was also calculated. Because of the similar steric and electronic properties of the N-benzyl and N-allyl substituents, the energies of the E and Z rotamers are comparable. Because steric repulsions with the geminal dimethyl groups at the a-carbon of the amide destabilize the planar amide geometry in the ground state, the amide bond rotation requires an activation free energy of 15.9 kcal/mol (TS4, with respect to 1a-Z), which is relatively low compared to other amide bond rotations (96). The computed barrier to the amide bond rotation of the radical intermediate 7 is even lower (11.1 kcal/mol with respect to 7-Z). The planar geometry of the radical center increases steric repulsions with the N-substituents, and thus destabilizes 7 and promotes the amide bond rotation. In addition, enzyme is known to catalyze amide bond rotation via several possible mechanisms, such as distortion, Brønsted acid/base catalysis, and nucleophilic catalysis (97, 98). Therefore, it was surmised that the Z/E isomerization of 1a and 7 may both be promoted within the enzyme active site. Although only the Z rotamer of the radical intermediate (7-Z) may undergo cyclization via the radical addition to the double bond, the E rotamer is expected to be quickly converted to the reactive Z rotamer either before or after the bromide atom abstraction. For simplicity, only the reactive Z rotamers are reported in the reaction energy profiles in the main text. The bromide atom abstraction pathway with the E rotamer was also calculated (FIG. 16). The activation free energy of bromine atom abstraction from the E rotamer E-1a ($^5$TS1-a) is very similar to that from the Z rotamer Z-1a ($^5$TS1-b), indicating that the rotamers of the amide have similar reaction rates in the bromine atom abstraction.

Conformational Search of Bromine Atom Abstraction (TS1) and Br Rebound Transition States (TS3)

The conformational space for transition states and intermediates were sampled using the conformer-rotamer ensemble sampling tool (CREST) program that uses the semiempirical tight-binding based quantum chemistry methods GFN2-xTB to perform metadynamic sampling (MTD) of conformers. iMTD-GC (iterative metadynamic sampling with genetic crossing approach) was used where an iterative root mean square deviation (RMSD) based metadynamic sampling is performed with an extra genetic z matrix crossing (GC) step at the end. The conformational sampling of stationary points was performed in the corresponding spin states. For ground state conformational sampling, no constrains were applied. For transition states sampling, the corresponding forming/breaking bonds were constrained at the transition state geometry obtained from DFT-optimized geometries with a force constant of 0.5 Hartree/Bohr$^2$. The structural similarity was then assessed by the RMSD threshold (1 Å) and energy threshold (10 kcal/mol). The structures obtained from conformational sampling were further optimized at the DFT level.

The CREST/xTB conformational sampling revealed a large conformational space for the transition states and intermediates. The overlays of resulting low-energy conformers (within 3.5 kcal/mol relative to the lowest-energy conformer at the DFT level) of the bromine atom abstraction transition state and the Br rebound transition state are shown in FIG. 16. The CREST/xTB conformational sampling produced 21 unique conformers for $^5$TS1 and 13 unique conformers for $^6$TS3 with different amide bond rotamers, and o-bond rotamers. In the most stable bromine atom abstraction transition state ($^5$TS1), has the amide bond of the substrate has the Z-conformation, which is the reactive rotamer that can directly undergo cyclization (via $^5$TS1-a). A transition state conformer $^5$TS1-b with inactive E-rotamer of amide moiety is only 1.4 kcal/mol higher in energy than $^5$TS1-a, indicating that the E-rotamer may also undergo bromine atom abstraction, albeit at a slightly lower rate. Similarly, multiple conformers with similar energies were located for the bromine rebound transition state, further support the conformational flexibility of studied model catalyst system in the absence of the enzyme environment.

Figure 17:
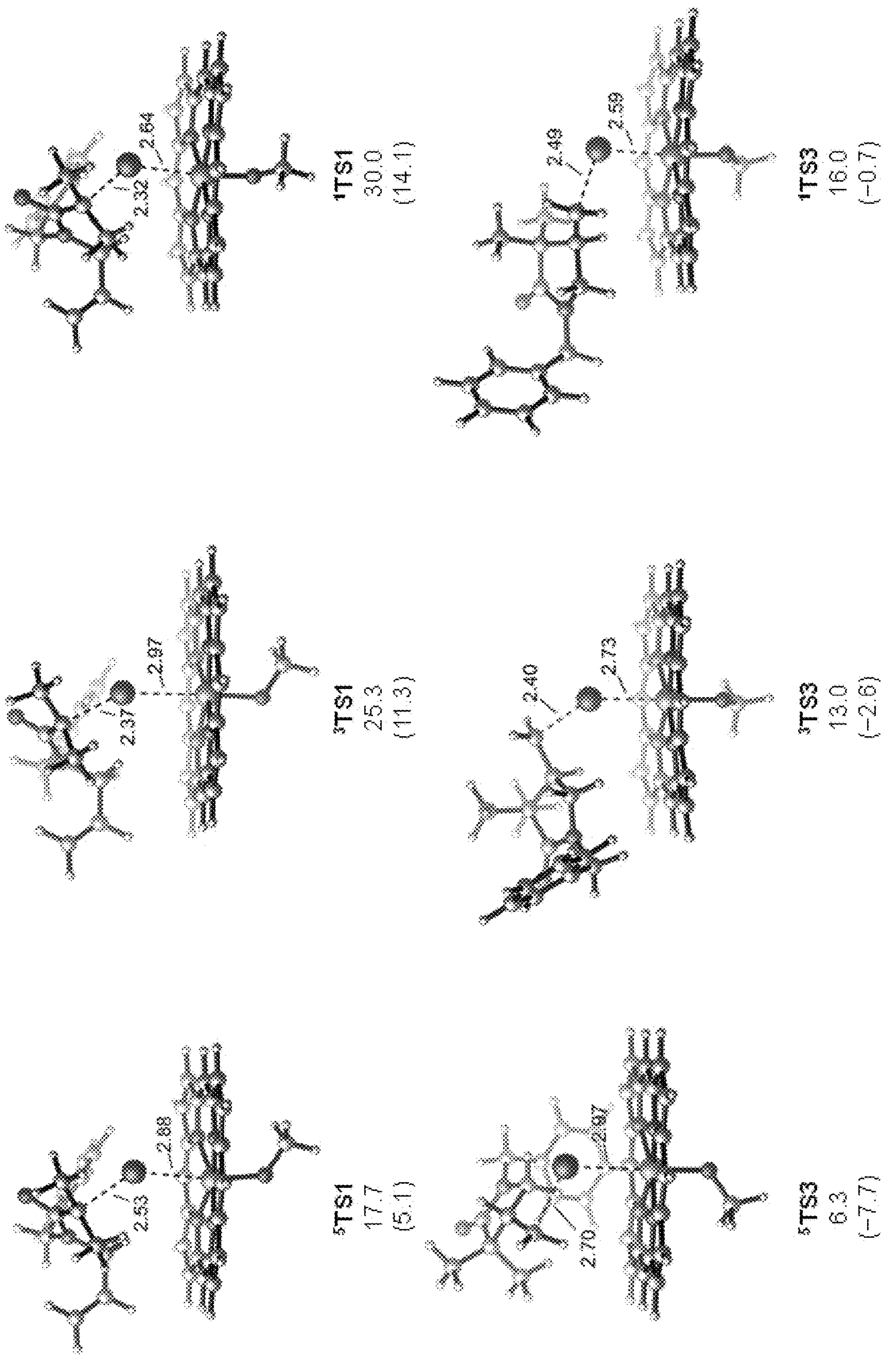
FIG. 17 provides a schematic of transition state structures of different spin states of TS1 and TS3 in accordance with various embodiments. All Gibbs free energies and enthalpies (in parentheses) are with respect to $^{5}4$ and 1a, in kcal/mol.

Following the same protocol, other spin states of transition states TS1 and TS3 were investigated (FIG. 17). The most stable transition state conformers of TS1 in different spin states have similar geometries. In TS3, the triplet and singlet transition states have shorter Fe—Br bond distances than the Fe—Br bond in the quintet of TS3. Due to the shorter Fe—Br distance, the benzyl group in the most stable transition state conformers of $^3$TS3 and $^1$TS3 rotated away from the porphine ligand to reduce steric repulsion.

Comparison of Fe-Porphine Catalyst With Cu(TPMA)+ ATRP Catalyst

To understand the origin of the effectiveness of the Fe-porphyrin catalyst in promoting the ATRC reaction, its electronic properties were directly compared with those of the Cu(TPMA)$^+$ catalyst, which is highly active in the alkyl halide activation in ATRP ($k_{act}$=4500 with ethyl 2-bromoisobutyrate in acetonitrile). The HOMO energies ($E_{HOMO}$) of both catalysts and the M(metal)-Br bond dissociation enthalpies [BDE(M-Br)] of the metal bromide intermediates at the (U)B3LYP-D3/6-311+G(d,p)-LANL2TZ (f)/SMD(chlorobenzene)//(U)B3LYP-D3/6-31G (d)-LANL2DZ level of theory were calculated. Those electronic parameters were reported to be the most important descriptors for the prediction of $k_{act}$ in Cu-ATRP. Although the bromine atom abstraction with Fe-porphine is thermodynamically less favorable by 4.8 kcal/mol due to the weaker Fe(III)-Br bond than the Cu(II)-Br bond, the higher HOMO energy kinetically promotes the ISET with the Fe(II) porphyrin complex. Overall, these electronic parameters are consistent with the high reactivities of both the Fe-porphine and Cu(TPMA)$^+$ catalysts in promoting bromine atom abstraction.

The Gibbs free energy of reaction was calculated for the DET pathway ($\Delta G_{DET}$) with the Fe-porphine and Cu(TPMA)$^+$ catalysts, respectively. The DET pathway is highly endergonic ($\Delta G_{DET}$=44.7 kcal/mol) with the Cu(TPMA)$^+$ catalyst in the non-polar solvent. The Cu(TPMA)$^+$ catalyst is known to have a low reactivity in promoting DET in polar solvents. These results indicate Cu(TPMA)$^+$ is even less reactive in DET in a less polar environment. On the other hand, the DET process with Fe-porphine is exergonic ($\Delta G_{DET}$=−4.2 kcal/mol), suggesting a thermodynamically more viable DET pathway in the reaction with the Fe-porphine catalysts.

TABLE 15

Electronic properties of Fe-porphyrin and Cu(TPMA)$^+$ catalysts.

[M] =

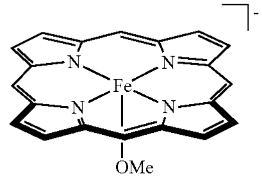

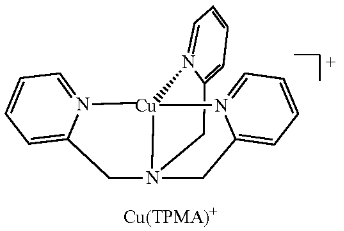

Cu(TPMA)$^+$ a. inner-sphere single electron transfer

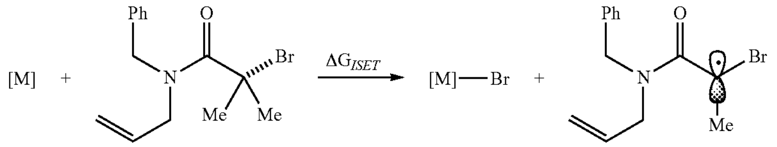

TABLE 15-continued b. outer-sphere single electron transfer

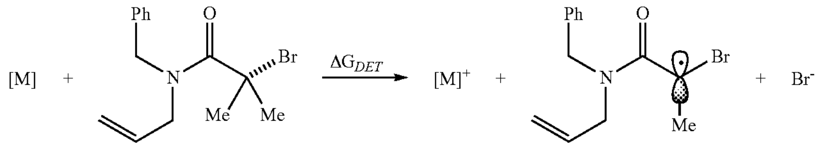

| | [5]4 | Cu(TPMA)$^+$ |
|---|---|---|
| BDE (M-Br, kcal/mol) | 50.8 | 54.6 |
| $E_{HOMO}$ (eV) | −3.3 | −5.6 |
| $\Delta G_{ISET}$ (kcal/mol) | 4.2 | −0.6 |
| $\Delta G_{DET}$ (kcal/mol) | −4.2 | 44.7 |

What is claimed is:

1. A method for conducting a controlled atom transfer radical addition or atom transfer radical cyclization reaction catalyzed by an unnatural metalloenzyme comprising:

- providing a first substrate including an alkyl halide moiety;
- providing a second substrate including an unsaturated carbon-carbon moiety;
- providing a metalloenzyme catalyst including a modified cytochrome P450 having an iron ion supported by a heme scaffold, wherein the metalloenzyme catalyst exerts enantiocontrol or diastereocontrol over the first and the second substrates; and
- combining the first substrate, the second substrate, and the metalloenzyme catalyst to react such that an atom transfer radical addition reaction or an atom transfer radical cyclization reaction occurs to afford a product wherein an alkyl group and a halogen atom of the alkyl halide moiety are installed across an unsaturated C—C bond of the unsaturated carbon-carbon moiety with a desirable enantiomer or and diastereomer outcome,
- wherein during at least a portion of the atom transfer radical addition reaction or an atom transfer radical cyclization reaction the metalloenzyme catalyst is in a ferrous state and undergoes single electron transfer with the first substrate to form a transient radical intermediate.

2. The method of claim 1, wherein the first substrate and the second substrate are within a single molecule.

3. The method of claim 1, wherein the first substrate and the second substrate are in two different molecules.

4. The method of claim 1, wherein the halogen atom is bromine, iodine, or chlorine.

5. The method of claim 1, wherein the unsaturated carbon-carbon moiety is an alkene or an alkyne.

6. The method of claim 1, wherein the iron ion is in a form of a Fe (II)/Fe (III) redox couple.

7. The method of claim 1, wherein the metalloenzyme catalyst is: $P450_{ATRAse1}$, $P450_{ATRAse2}$, $P450_{ATRAse3}$, $P450_{ATRAse4}$, or an earlier variant from the $P450_{ATRAse1}$, $P450_{ATRAse2}$, $P450_{ATRAse3}$, or $P450_{ATRAse4}$ evolutionary lineage.

8. A metalloenzyme catalyst comprising a modified *Bacillus megaterium* P450 (CYP102A1) having one or more of the following mutations: A82T, L181F, L181V, 1263Q, I263L, E267A, A268G, H266T, T327I, P327C, T327V, A330T, S400A, L436T, L437I, L437F, T438Q or S438Y.

9. The metalloenzyme catalyst of claim 8, wherein the modified P450 has one or more of the following mutations: A82T, L181F, 1263Q, H266T, or T327I.

10. The metalloenzyme catalyst of claim 8, wherein the modified P450 has the following mutations: A82T, L181F, I263Q, H266T, and T327I.

11. The metalloenzyme catalyst of claim 8, wherein the modified P450 has a sequence comprising SEQ ID No. 1.

12. The metalloenzyme catalyst of claim 8, wherein the modified P450 has one or more of the following mutations: L181V, P327C, S400A, L436T or T438Q.

13. The metalloenzyme catalyst of claim 8, wherein the modified P450 has the following mutations: L181V, P327C, S400A, L436T and T438Q.

14. The metalloenzyme catalyst of claim 8, wherein the modified P450 has a sequence comprising SEQ ID No. 2.

15. A metalloenzyme catalyst of claim 8, wherein the modified P450 has one or more of the following mutations: A82T, L181F, I263Q, E267A, T327I, L437I or S438Y.

16. The metalloenzyme catalyst of claim 8, wherein the modified P450 has the following mutations: A82T, L181F, I263Q, E267A, T327I, L437I and S438Y.

17. The metalloenzyme catalyst of claim 8, wherein the modified P450 has a sequence comprising SEQ ID No. 3.

18. The metalloenzyme catalyst of claim 8, wherein the modified P450 has one or more of the following mutations: A82T, L181V, 1263L, A268G, T327V, A330T, L437F or S438Q.

19. The metalloenzyme catalyst of claim 8, wherein the modified P450 has the following mutations: A82T, L181V, I263L, A268G, T327V, A330T, L437F and S438Q.

20. The metalloenzyme catalyst of claim 8, wherein the modified P450 has a sequence comprising SEQ ID No. 4.

* * * * *